United States Patent
van Buskirk et al.

(10) Patent No.: US 10,334,853 B2
(45) Date of Patent: Jul. 2, 2019

(54) COMPOSITIONS AND METHODS FOR TREATING ECTOPARASITE INFESTATION

(71) Applicant: Larada Sciences, Inc., Murray, UT (US)

(72) Inventors: Gregory van Buskirk, Danville, CA (US); Kelly J. Brodbeck, Santa Barbara, CA (US)

(73) Assignee: Larada Sciences, Murray, UT (US)

(*) Notice: Subject to any disclaimer, the term of this patent is extended or adjusted under 35 U.S.C. 154(b) by 0 days.

(21) Appl. No.: 15/131,607

(22) Filed: Apr. 18, 2016

(65) Prior Publication Data

US 2018/0070593 A1  Mar. 15, 2018

Related U.S. Application Data

(63) Continuation-in-part of application No. 29/559,554, filed on Mar. 29, 2016, now Pat. No. Des. 817,547.

(51) Int. Cl.

| A61K 9/00 | (2006.01) |
|---|---|
| A61P 33/14 | (2006.01) |
| A61K 8/25 | (2006.01) |
| A01N 55/00 | (2006.01) |
| A01N 25/30 | (2006.01) |
| A61K 31/80 | (2006.01) |
| A61K 47/18 | (2017.01) |
| A61K 9/06 | (2006.01) |

(52) U.S. Cl.
CPC ............ *A01N 55/00* (2013.01); *A01N 25/30* (2013.01); *A61K 9/0017* (2013.01); *A61K 9/06* (2013.01); *A61K 31/80* (2013.01); *A61K 47/18* (2013.01); *A61P 33/14* (2018.01)

(58) Field of Classification Search
None
See application file for complete search history.

(56) References Cited

U.S. PATENT DOCUMENTS

| 5,714,137 | A | * | 2/1998 | Trinh | ........................ | A61L 9/01 |
| | | | | | | 424/76.1 |
| 5,858,383 | A | | 1/1999 | Precopio | | |
| 5,981,605 | A | * | 11/1999 | Thomsen | ................. | A61K 8/34 |
| | | | | | | 514/724 |
| 5,985,294 | A | | 11/1999 | Peffley | | |
| 6,200,554 | B1 | | 3/2001 | Yeoh et al. | | |
| 6,610,280 | B2 | | 8/2003 | Ainger et al. | | |
| 7,829,551 | B2 | | 11/2010 | Ansell | | |
| 8,097,602 | B1 | | 1/2012 | Holzer | | |
| 8,252,271 | B2 | | 8/2012 | Singer et al. | | |
| 8,530,451 | B2 | | 9/2013 | Cooper | | |
| 9,040,029 | B2 | | 5/2015 | Hoffmann et al. | | |
| 2001/0043912 | A1 | | 11/2001 | Michael | | |
| 2002/0182161 | A1 | | 12/2002 | Ainger et al. | | |
| 2003/0027792 | A1 | | 2/2003 | Ansell | | |
| 2003/0040504 | A1 | * | 2/2003 | Gans | ...................... | A01N 27/00 |
| | | | | | | 514/72 |
| 2003/0165453 | A1 | | 9/2003 | Nguyen et al. | | |
| 2003/0228342 | A1 | * | 12/2003 | Ping | ....................... | A01N 49/00 |
| | | | | | | 424/405 |
| 2005/0197479 | A1 | * | 9/2005 | Pavlin | ...................... | A61K 8/02 |
| | | | | | | 528/64 |
| 2006/0121073 | A1 | | 6/2006 | Goyal et al. | | |
| 2007/0184008 | A1 | | 8/2007 | Rogers et al. | | |
| 2007/0204871 | A1 | | 9/2007 | Singer et al. | | |
| 2007/0212382 | A1 | | 9/2007 | Boskamp et al. | | |
| 2008/0193387 | A1 | * | 8/2008 | De Wolff | ............... | A61K 36/23 |
| | | | | | | 424/47 |
| 2008/0312085 | A1 | * | 12/2008 | Kordes | ................ | C07D 417/12 |
| | | | | | | 504/247 |
| 2010/0227010 | A1 | * | 9/2010 | Jones | ..................... | A01N 37/02 |
| | | | | | | 424/747 |
| 2011/0092455 | A1 | | 4/2011 | Ansell | | |
| 2011/0132388 | A1 | | 6/2011 | Nguyen et al. | | |
| 2012/0071444 | A1 | | 3/2012 | Cooper | | |
| 2012/0093949 | A1 | | 4/2012 | Steinberg | | |
| 2012/0276035 | A1 | | 11/2012 | Lehman | | |
| 2013/0018016 | A1 | | 1/2013 | Ueck | | |
| 2013/0330291 | A1 | | 12/2013 | Hoffman et al. | | |
| 2014/0072523 | A1 | | 3/2014 | Battermann et al. | | |
| 2015/0342858 | A1 | | 12/2015 | Tamareselvy et al. | | |

OTHER PUBLICATIONS

I.F. Burgess, "The mode of action of dimethicone 4% lotion against head lice, Pediculus capitis," MBC Pharmacology, 2009, 9-3.
Material Safety Data Sheet, Polydimethylsiloxane, Element 14* PDMS 350-E, Momentive Performance Materials, Inc., Ver. 1.3, Waterford, NY (Jul. 19, 2012).
Safety Data Sheet, Dow Corning® 200 Fluid, 100 CST, Ver. 2.2. SDS 1489116-00008, Dow Corning, Auburn, MI (Mar. 2, 2015).
Safety Data Sheet for Polydimethylsiloxane, Product No. 1546300, CAS-No. 9016-00-6, Version 5.0, Revision Date Sigma-Aldrich (Dec. 12, 2016).

(Continued)

*Primary Examiner* — Robert T. Crow
*Assistant Examiner* — John P Nguyen
(74) *Attorney, Agent, or Firm* — Matthew D. Thayne; Thayne and Davis LLC

(57) ABSTRACT

Compositions suitable for topical use to treat ectoparasite infestations are described. The compositions are suitable for use on the hair of humans or animals, without the need for pharmaceuticals or medicaments. The compositions are essentially nonaqueous and non-Newtonian, such that the compositions can be controllably delivered either manually or through use of a dispensing means. One such exemplary dispenser/applicator is described. Although the compositions are otherwise substantially free of water, they exhibit good risibility characteristics and pseudoplastic rheology. Methods for the use of the nonaqueous compositions and kits containing the compositions are also presented.

13 Claims, 2 Drawing Sheets

(56) References Cited

OTHER PUBLICATIONS https://en.wikipedia.org/wiki/Polydimethylsiloxane (downloaded Aug. 29, 2017).
https://en.wikipedia.org/wiki/Head_louse (downloaded: Sep. 1, 2017).
https://en.wikipedia.org/wiki/Thixotropy (downloaded: Sep. 1, 2017).
International Preliminary Report on Patentability for PCT/US2017/028019, dated Nov. 28, 2018, 16 pgs.

* cited by examiner

COMPOSITIONS AND METHODS FOR TREATING ECTOPARASITE INFESTATION

RELATED APPLICATIONS

This application is a continuation-in-part of U.S. patent application Ser. No. 29/559,554, filed 29 Mar. 2016, the content of which is incorporated herein in its entirety.

BACKGROUND

1. Technical Field

The instant disclosure relates generally to compositions and methods for killing ectoparasites. More particularly, the instant disclosure concerns nonaqueous, topical formulations for use in the treatment of conditions of inspect pest infestations on the hair of an animal or a human.

2. Discussion of Related Art

The literature is replete with treatments to eliminate ectoparasites, or parasites that live on or in the skin of humans and other animals, such as lice, ticks and fleas. Treatments that are used to kill head lice, in particular, are termed pediculicides. Many of these treatments incorporate nerve toxicants, such as pyrethrins, to kill parasites. However, such toxicants can not only present hazards to users of such treatments, but long-term use of such toxicants actually has led to some parasites developing an immunity to the substance. Indeed, the continued use of pyrethrin in the case of head lice has led to so-called "super lice," which have now been found in at least 35 states of the United States.

Polydimethylsiloxanes or PDMS, also known as dimethicones or silicon fluids, have been found to be very effective in the treatment of lice, especially head lice. See I. F. Burgess, 2009. *"The mode of action of dimethicone 4% lotion against head lice, Pediculus capitis,"* BMC Pharmacology 2009, 9:3. The action pathway of PDMS against parasites is apparently to find entry into their spiracles. Spiracles are structural openings on the surface of insects, which function as entry points to their respiratory system and regulate moisture within the organism. It is believed that PDMS blocks respiration and/or moisture excretion by the parasite, leading to its death within minutes. Such action against a parasite—relying on an innate structural feature rather than on a toxicant such as pyrethrins—virtually ensures that immunity against the treatment cannot occur. Burgess also reports that lice are able to survive immersion in water for several hours, presumably tolerating long periods without oxygen. Accordingly, specific experimental investigations of the potential for suffocation by various preparations have not been shown to be feasible.

Numerous disclosures have taught the use of PDMS in hair treatments, for example hair conditioners, as well as use as pediculicides. However, general use of PDMS preparations as consumer-acceptable pediculicides is not straightforward, due to their basic properties such as hydrophobicity, general difficulty in formulation and flow characteristics. In general, hair treatments such as hair conditioners or shampoo/conditioners that contain PDMS contain water, which has been demonstrated to subvert the action of PDMS against parasites. Further, pediculocidal preparations have been described that are difficult to control due to the rheological nature of PDMS. In general, they tend to flow uncontrollably during dispensing. Further, once applied, the hydrophobic nature of PDMS makes such preparations difficult to rinse from hands and hair, thus making cleanup an unpleasant task. Both physical flow and control of a composition during use as well as cleanup of the composition following treatment are therefore two common problems that have not been satisfactorily addressed in the past.

For example, U.S. Pat. No. 5,858,383 to Precopio claims compositions for topical treatment of ectoparasites on animal skin, comprising at least one skin compatible surface-active agent. No mention is made of incorporating PDMS into the compositions, and examples comprise at least 5 wt. % water, the presence of which would allow lice to survive during and after treatment. U.S. Pat. No. 7,829,551 to Ansell describes compositions for controlling lice on a human subject, comprising 95.5-97.5 wt. % of a volatile siloxane and 2.5-4.5 wt. % of a non-volatile siloxane having a viscosity of 100,000 centistokes. The cyclic volatile siloxane, cyclomethicone, functions as a liquid carrier for the composition, but being volatile and thus evaporative, would not remain on a parasite. Moreover, cyclomethicones, having a low flash point, are disfavored for use in commerce in the U.S. due to their volatility. Other references such as U.S. Publ. No. 20110092455 to Ansell, U.S. Pat. No. 9,040,029 B2 to Hoffman, et al., and U.S. Publ. No. 20120276035 to Lehman all include cyclomethicone-containing compositions that are similarly disadvantages. They contain significant quantities of water, which would not be conducive for use as a pediculicide. Moreover, there is no mention of flow characteristics, and risibility is likely poor.

While U.S. Pat. No. 8,097,602 to Holzer does not contain cyclomethicone, it describes compositions suitable for treating body insect infestations that contain 10-75 wt. % by volume of a siloxane and a surfactant. There is no mention of the viscosity or pseudoplasticity of the compositions, and flow would be uncontrollable, but the compositions can include water, which would allow lice to survive during and after treatment. Furthermore, Holzer's formulations are difficult to extract from the hair, and several washes with a shampoo product are required.

U.S. Pat. No. 8,530,451 B2 to Cooper describes an ectoparasiticidal composition comprising a mixture of a carrier and an active with an emulsifying agent, the carrier comprising a nonvolatile low viscosity siloxane and a nonvolatile high viscosity siloxane. However, both the low viscosity siloxane and the high viscosity siloxane have a closed cup flash point of at least 100° C. These compositions will have constant viscosity as a function of stress, and therefore will not have desirable, controllable flow characteristics. Moreover, these compositions would be very difficult to rinse out of the hair and off hands following application and treatment.

U.S. Publ. No. 20060121073 to Goyal, et al., describes ectoparasitic treatment compositions comprising an insecticide, specific classes of organic solvents and at least one viscosity-modifying polymer. While they recognize that compositions should have limited water, they describe formulation pH, a property of aqueous systems, and the viscosity-modifying polymers used are only activated in the presence of water. As stated above, the presence of water can allow lice to survive during and after treatment. Another disadvantage is the likely difficulty in rinsing the composition out of the hair and off hands following application and treatment.

U.S. Ser. No. 20070212382 to Boskamp, et al., describes compositions for killing ectoparasites and/or their ova, comprising 30-49 wt. % of a low viscosity linear polysiloxane having a viscosity less than 10 cSt, 35-65 wt. % of a higher viscosity linear polysiloxane having a viscosity greater than 90 cSt, and at least one spreading agent. The application does not mention rheology of the compositions, and thus controllability of the composition is uncertain. Moreover, no surfactants are mentioned, and thus the compositions would be difficult to rinse from hands and hair following application and treatment.

U.S. Publ. No. 20120093949 to Steinberg describes a treatment composition against lice, comprising 19-80 wt. % olive oil, 19-80 wt. % dimethicone, 0-2 wt. % rosemary oils, and 0.5-10 wt. % beeswax. Beeswax is noted to increase the cohesiveness and thickness of the treatment mixture, and may also thicken the mixture so that it is less messy when applied to the hair or scalp and make the mixture more viscous. However, lack of a surfactant would likely make this composition difficult to rinse from hair and hands following application and treatment.

U.S. Publ. No. 20130018016 to Ueck describes compositions for killing ectoparasites or their ova, comprising at least one volatile non-polar organic solvent, 1-10 wt. % of at least one spreading agent, and 35-65 wt. % of at least one polysiloxane having a viscosity of greater than 90 cSt. The application does not mention whet viscosity or pseudoplasticity, whether the composition is viscous or has pseudoplasticity, and so it would flow uncontrollably through the dispensing device. Additionally, the organic solvents mentioned are hydrocarbons, which are rather drying to skin. Further, no surfactants are mentioned, meaning that the compositions would be difficult to rinse off from hands and hair following application and treatment.

U.S. Pat. No. 5,985,294 to Peffley describes leave-in hair styling formulations, comprising 0.01-20 wt. % of a non-silicone containing polymer suitable for hair styling, 0.01-10 wt. % of an organopolysiloxane microemulsion, a surfactant system for dispersing the organopolysiloxane in the microemulsion, and a carrier. The carrier comprises 3-99 wt. % of a first solvent that can include water; water-soluble organic solvents; organic solvents which are strongly to moderately strong in hydrogen-bonding parameter; and mixtures thereof. No product viscosity or pseudoplasticity is mentioned, and so it is likely that the composition could not be controllably delivered. Risibility is anticipated to be difficult to remove following treatment. Furthermore, Peffley discusses 3-99 wt. % water, and all examples have at least 70 wt. % water; the presence of which would allow lice to survive during and after treatment.

U.S. Pat. No. 6,200,554 to Yeoh, et al., describes a conditioning shampoo composition comprising about 5-50 wt. % by weight of a detersive surfactant, about 0.1-10 wt. % by weight of an ethoxylated fatty alcohol having a fatty alcohol moiety, 0.01-20 wt. % by weight of dispersed particles of a nonvolatile silicone hair conditioning agent, 0.1-10 wt. % of a water-activated suspending agent, and 10-95.79 wt. % by weight water. As their compositions all rely on water to build viscosity, they are not suitable for use as pediculicides.

U.S. Pat. No. 6,610,280 B2 to Ainger, et al., describes hair treatment compositions containing droplets comprising a silicone component, wherein the silicone component in each droplet consists of from 50-95 wt. % by weight of the silicone component of a first silicone having a viscosity of at least 100,000 mm$^2$/sec or 100,000 cps at 25° C., and from 5-50 wt. % by weight of the silicone component of a second silicone which is functionalized. The silicone components are suspended droplets, rather than uniformly distributed throughout the matrix. Indeed, the extremely high viscosity of major component, as described, would be difficult to dispense were it to be uniformly distributed. There is no indication that the bulk composition has any significant viscosity and/or pseudoplasticity, and thus it is likely that such a composition would flow uncontrolledly. Similarly, U.S. Pat. No. 8,252,271 B2 to Singer, et al., describe leave-in hair styling compositions containing at least one silicone elastomer, a nonaqueous polar solvent and a cosmetically acceptable co-solvent. With at least 30 wt. % water for Ainger, et al., and about 48 wt. % water for Singer, et al., neither one is recommended for use as a pediculicide.

U.S. Publ. No. 20070184008 to Rogers, et al., describes a topical Shea butter derivate-based ingredient, but there is no mention of the ability to be controllably delivered in a nonaqueous matrix, or to be readily rinsed from hands and hair following application and treatment. Similarly, U.S. Publ. No. 20110132388 to Nguyen, et al., describes hair protection compositions comprising at least one silicone and at least one film-forming polymer, but the compositions comprise about 83 wt. % water and would therefore allow lice to survive during and after treatment.

U.S. Publ. No. 20140072523 to Battermann, et al., describes leave-in hair care compositions comprising at least one ester oil, a silicone, an acrylic acid derivative, and water. Similarly, U.S. Publ. 20150342858 to Tamareselvy, et al. also describes a hair conditioning cleansing composition comprising at least one detersive surfactant, a silicone conditioning agent, water, and a stabilizer/thickener polymer and include up to 75 wt. % water. Neither of the foregoing would be suitable as a pediculicide due to the presence of water, which would allow lice to survive during and after treatment.

SUMMARY OF THE DISCLOSURE

In the past, many lice-treatment compositions have been found to be drippy, messy affairs when treating a subject that is experiencing a lice infestation. This has resulted in great dissatisfaction with many such products. A number of products are known that contain PDMS or polydimethylsiloxanes, but they can be very difficult to rinse off with water following treatment. Often, several washings with soap are necessary in order to remove the dimethicone to a satisfactory degree. None of the commercial products currently on the market have been demonstrated to resolve all of these issues, and yet be effective for the control of head lice. It would be particularly useful to have a nonaqueous product for controlling head lice, which is essentially free of water to prevent the head lice from surviving the treatment. Further, it is desirable for such a product to exhibit a rheology such that the application of the composition is readily controllable during application of the product, either manually or via the use of dispensing means, and further which product is easily rinsed off following treatment. It would be further preferred that the ingredients used in the product are non-irritating, as the product will be applied to hair and scalp of human subjects, especially children. Having non-irritating ingredients is of importance particularly in the case of children, where more than one treatment is often necessary.

Lice infestations, a major problem throughout the world, may be characterized by different locations on the body on which different species of lice prefer to feed. Louse species include *Pediculus humanus* capitis or head lice, *Pediculus humanus* corporis or body lice and *Phthirus pubis* or pubic lice, sometimes called "crabs." One form of ectoparasites, that is head lice, *Pediculus humanus capitis*, spend their entire life on the human scalp and feed exclusively on human blood. See https://en.wikipedia.org/wiki/Head- _louse. All stages of head lice are blood feeders and they bite the skin four to five times daily to feed. They inject saliva, which contains an anti-coagulant, and suck blood from the host animal. The human body has an allergic reaction to louse saliva, resulting in significant itching and discomfort during the infestation.

While head lice have not been shown definitively to be the vectors of any known diseases, at minimum they can result in secondary infections that result from scratching at bites. It has further been suggested that bites can result in excoriations, secondary impetiginization, pyoderma with or without hair loss, cervical lymphadenopathy, conjunctivitis, fever, malaise, and occasionally a diffuse morbilliform hypersensitivity eruption. See Martinez-Diaz, G. J. and A J. Mancini, "Head Lice: Diagnosis and Therapy," Dermatology Nursing; July/August 2010, 22:4, p. 2.

Head lice are easily transmittable between subjects, and as a result are subject to various eradication campaigns, especially in schools and homes. There have been numerous products on the market for control of head lice infestation. Historically, these products contained pyrethrins, a class of organic compounds normally derived from *Chrysanthemum cinerariifolium*, which have potent insecticidal activity by targeting the nervous systems of insects, including head lice. See https://en.wikipedia.org/wiki/Pyrethrin. Unfortunately, head lice have become increasingly resistant to pyrethrins over time, necessitating the search for alternate means for controlling them and their infestations. Furthermore, many individuals are sensitive to contact with pyrethrins on their skin, a factor that has increasingly provided incentive to seek out alternate compositions for combating ectoparasites.

ELEMENT LIST FOR FIG. 2

Figure 1:
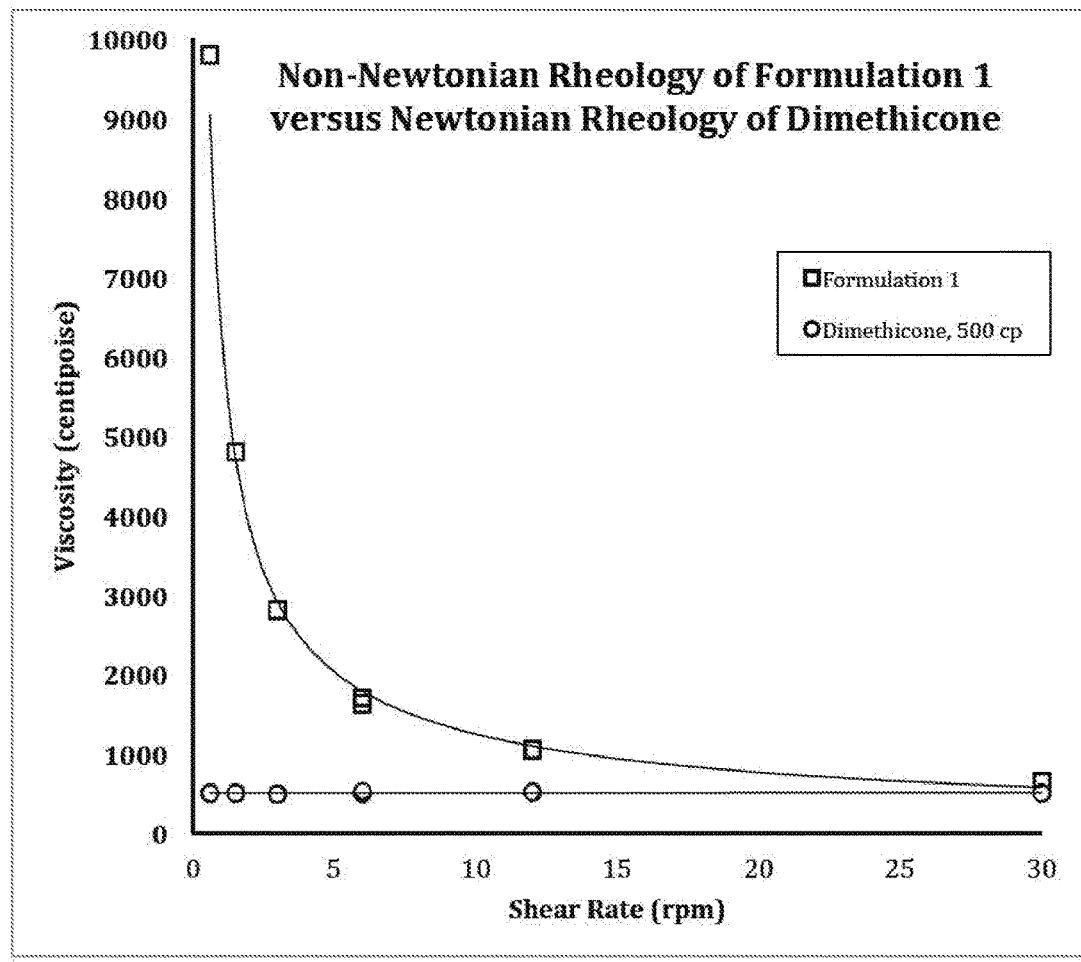
FIG. 1 is a graph of viscosity versus shear rate for a formulation disclosed herein as compared to a known standard.
Figure 2:
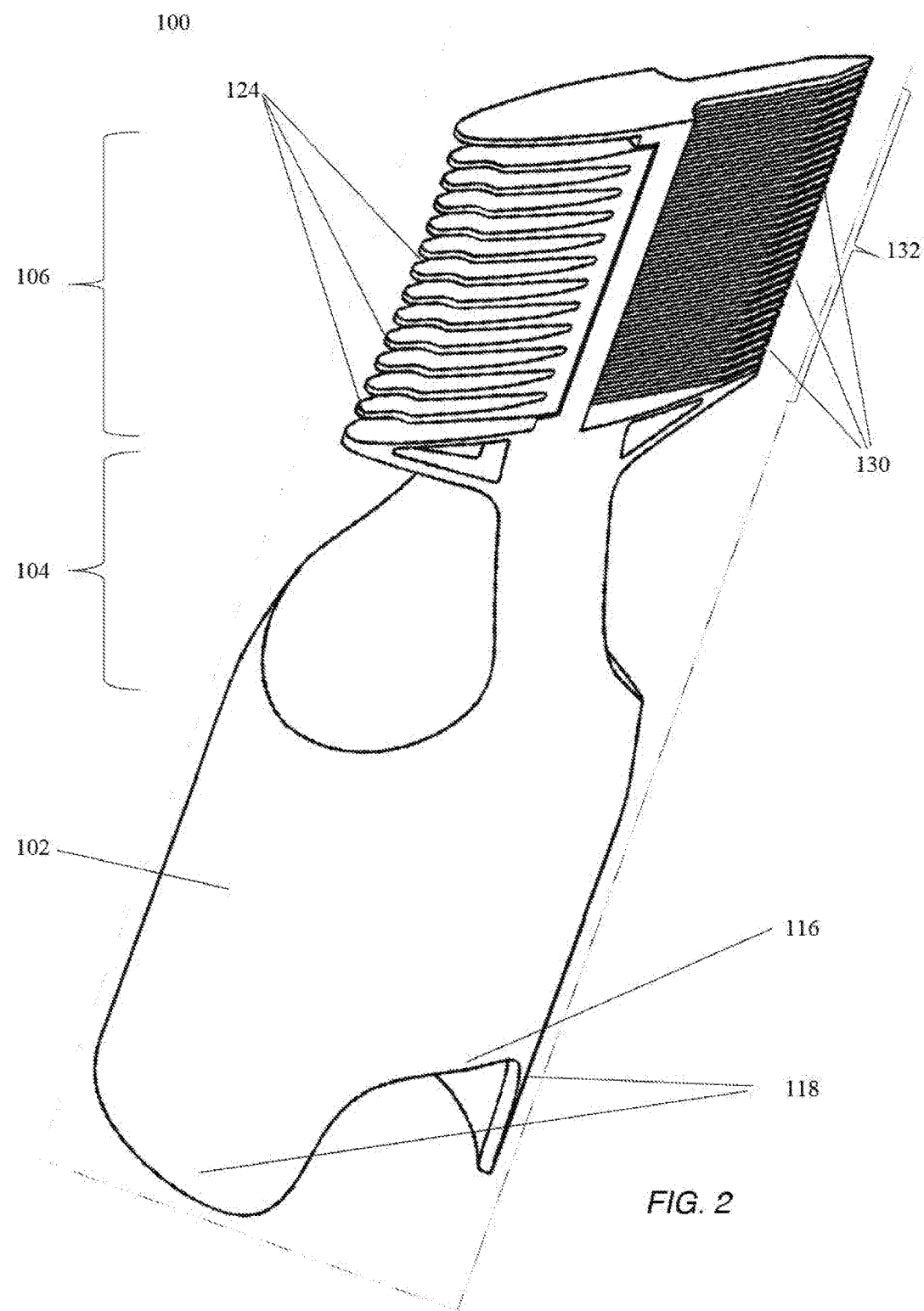
FIG. 2 is a top, left front perspective view of one type of dispenser or applicator that may be used with a topical composition according to one embodiment of the disclosure.

100 Dispenser applicator
102 Handle or grip portion
104 Contour region
106 Applicator region
108 First attachment means
110 Attachment component
112 Container
114 Second attachment means
116 Cutouts
118 Leg sections
120 Channel
122 Openings
124 Teeth
126 First facing surface
128 Second facing surface
130 Tines
132 Rake portion
134 Comb portion Definitions Words and terms of art that are used herein are to be understood in terms of the definitions provided below or in the discussions which follow for use in this specification, and then as needed as one skilled in the relevant art would ordinarily define the words and terms. All references to patents, patent publications and published articles mentioned herein are hereby incorporated in their entirety by reference.

"At least one" as used herein means one or more, and thus includes individual components as well as mixtures/combinations.

"Bingham plastics" or "Bingham liquids" are fluids that behave like solids under static conditions (see https://en.wikipedia.org/wiki/Non-Newtonian_fluid#Bingham_plastic). A finite yield stress must be applied to the fluid before flow commences. This force is called yield value. Once the yield value is exceeded and flow begins, such fluids may display Newtonian, pseudoplastic or dilatant flow characteristics.

"Dimethicone", otherwise known as polydimethylsiloxane or silicone, describes a group of polymeric organosilicon compounds. Lower molecular-weight members of this class are known to exhibit Newtonian flow characteristics, that is, their viscosity is not influenced by shear rate. See http://www.dowcorning.com/content/discover/discoverchem/si-rheology.aspx for information on rheology and Newtonian flow characteristics. For information about shear rate, see: http://www.dowcorning.com/content/discover/discoverchem/si-rheology.aspx.

"Keratinous fiber" means a substance primarily comprised of keratin, a fibrous structural protein found, inter alia, in human skin and hair.

"Newtonian fluids" exhibit in which the ratio of shear stress to shear rate is constant and its viscosity is independent of the shear rate applied to it. Such fluids will tend to flow even in the absence of a stress, such as squeezing of a dispensing container, though the rate of flow will depend on its intrinsic viscosity.

The terms "nonaqueous" or "essentially nonaqueous" when used with reference to the compositions presented herein, are understood to indicate that the composition contains less than about 5 wt. % water, preferably less than about 3 wt. % water, more preferably less than about 2.0 wt. % water, and most preferably less than about 1.0 wt. % water.

"Non-Newtonian fluids" exhibit rheology in which the ratio of shear stress to shear rate is not constant. Shear-thinning fluids exhibit an apparent viscosity at high shear rates that is less than the viscosity exhibited at low shear rates. Shear-thickening fluids exhibit an apparent viscosity at high shear rates that is greater than the viscosity exhibited at low shear rates. Especially with respect to the nonaqueous topical compositions described herein, the terms "favorable non-Newtonian rheology" or "desirable non-Newtonian rheology" is understood to indicate that, due to shear thinning, the compositions will essentially stay in place in the absence of an external force, yet they will flow in the presence of an external force, such as the squeezing of a dispensing container. Said differently, once an external force is applied, such as squeezing, the fluid will commence flowing until the stress has been removed. Once the stress is removed, flow of the compositions described herein will cease to flow.

"Pseudoplastic" is a term applied to rheology, denoting a reduction of viscosity when shear forces are applied. It is sometimes also called shear-thinning. The stronger a shear stress that is applied to a pseudoplastic compound, mixture, or composition, the greater is the decrease in viscosity.

"Rheology" is the science of flow and deformation of matter, and describes the interrelationship among force, deformation and time. As used herein, favorable rheology, acceptable rheology, or good rheological characteristics are understood to indicate that the disclosed compositions, while rather thick and viscous if standing, may nonetheless be made to move or flow without application of a great deal of force.

"Silicone" means polydimethylsiloxane, otherwise known as dimethicone, describes a group of polymeric organosilicon compounds. Lower molecular-weight members of this class are known to exhibit Newtonian flow characteristics, that is, their viscosity is not influenced by shear rate (see http://www.dowcorning.com/content/discover/discoverchem/si-rheology.aspx).

"Viscosity" of a fluid is the measure of a fluid's ability to resist deformation by shear or tensile stresses, and is defined as the ratio of shear stress to shear rate. A fluid that has high viscosity will pour slowly as a function of time. A fluid that has low viscosity will pour quickly as a function of time. Viscosity, however, is not necessarily constant (see definitions of "Newtonian" and "non-Newtonian" fluids.

As used herein, the units centipoise (cps), milliPascal seconds (mPas) and centiStokes (cSt) are understood to have their standard engineering meanings, where 1 cps is equivalent to 1 mPas, which is also equivalent to 1 cSt. As these are equivalent terms, use of any one expression is also understood to represent the same quantity as if it were expressed in any of the other, equivalent forms.

DETAILED DESCRIPTION OF THE DISCLOSURE

Other than in the operating examples, or where otherwise indicated, all numbers expressing quantities of ingredients used herein are to be understood as modified by the term "about." Where provided, all amounts of ingredients are understood to be expressed in terms of weight percent or percent by weight, abbreviated as wt. %, unless indicated otherwise.

Nonaqueous antiparasitic compositions are disclosed that find particular application for use in treating topical infestations of insect pests on the surface hairs of a human subject. These nonaqueous compositions are comprised of an active ingredient comprising a polydimethylsiloxane or PDMS, also called a silicone, silicone oil or dimethicone. Until now, the ability to control solutions containing PDMS in nonaqueous matrices has not been demonstrated, nor to be easily rinsed during and following application. Among other functions, Polydimethylsiloxanes or PDMS have been shown to be quite effective in eliminating head lice. See https://en.wikipedia.org/wiki/Polydimethylsiloxane. PDMS are optically clear, and, in general, inert, non-toxic, and non-flammable. Their use ranges from contact lenses and medical devices to elastomers. PDMS-containing products are generally aqueous-based and readily pourable. Accordingly, such compositions may be characterized as Newtonian liquids. A Newtonian liquid is one that tends to flow, whether or not subject to an external force.

In addition to an active ingredient, the antiparasitic compositions of the instant disclosure also include an emulsifier and a nonaqueous solvent. Advantageously, a thickener is also used. Other components may also be used with the formulations described herein, in order to impart certain characteristics to the formulations that may make them more desirable from a consumer perspective. Additional components contemplated for use with the antiparasitic compositions described herein include fragrances, colorants, bittering agents, and so forth.

Exemplary embodiments according to the present disclosure will be described in detail with reference to any accompanying drawings. Terms may be specially defined in consideration of configurations and operations of the present disclosure, and may vary depending on the intention or usual practice of a user or operator. These terms should be defined based on the content throughout the present specification. The spirit of the present disclosure is not limited to the suggested exemplary embodiments; those skilled in the art who understand the spirit of the present disclosure may easily carry out other exemplary embodiments within the scope of the same spirit, and of course, the other exemplary embodiments also belong to the scope of the present disclosure.

It is to be understood that both the foregoing general description and the following detailed description are exemplary and explanatory only and are not restrictive of the claims that follow. As used herein, the use of the singular includes the plural unless specifically stated otherwise. As used herein, "or" means "and/or" unless stated otherwise. Furthermore, use of the term "including" as well as other forms such as "includes," and "included," is not limiting. The sectional headings used herein are for organizational purposes only and are not to be construed as limiting the subject matter described.

In one aspect therefore, a nonaqueous composition for the control and elimination of ectoparasites is disclosed, that comprises:
  a. at least one active ingredient;
  b. at least one emulsifier; and
  c. at least one nonaqueous solvent, or at least one thickener, or at least one nonaqueous solvent and at least one thickener;
wherein the active ingredient comprises a dimethicone.

In another aspect, the present disclosure concerns a nonaqueous antiparasitic composition, comprising:
  a. at least one active ingredient;
  b. at least one emulsifier;
  c. at least one nonaqueous solvent; and
  d. at least one thickener;
wherein the active ingredient comprises a dimethicone or polydimethylsiloxane, the composition exhibits good rheological characteristics, and a majority of ectoparasites are killed within thirty minutes after administration of the composition, preferably within twenty minutes after administration of the composition, and most preferably within ten minutes after administration of the composition.

In a different aspect, a topical composition is disclosed for the treatment and elimination of pests, comprising:
  a. at least one active ingredient;
  b. at least one emulsifier;
  c. at least one nonaqueous solvent; and
  d. a thickener;
wherein the emulsifier is a surfactant and the composition is essentially nonaqueous, possesses non-Newtonian rheology, and readily rinses from the hair of a subject to which it is applied.

In a further aspect, a topical composition is disclosed for the treatment and elimination of an insect infestation from the hair of an animal or a human being, that comprises:
  a. an active ingredient;
  b. a surfactant;
  c. a nonaqueous solvent; and
  d. a thickener;
  wherein:
  the active ingredient comprises a dimethicone;
  the surfactant is a nonionic surfactant;

the solvent is selected from among the group consisting essentially of butyrates, myristates, propylene glycol and combinations thereof;

the thickener is selected from among the group consisting essentially of polyamides, silica, clays, and combinations thereof; and the composition is essentially nonaqueous, possesses non-Newtonian rheology and is therefore said to be non-Newtonian, and easily rinses from the hair or surface of a subject to which it is applied.

In a still further aspect, the instant disclosure is directed to a method of killing ectoparasites on a subject, the method comprising:

a. topically administering a nonaqueous composition to a subject, wherein the composition comprises:
1) at least one active ingredient;
2) at least one emulsifier; and
3) at least one nonaqueous solvent, or at least one thickener, or at least one nonaqueous solvent and at least one thickener;

wherein the active ingredient comprises a polydimethylsiloxane.

In yet a still further aspect, the instant disclosure is directed to a method of killing ectoparasites on a subject, the method comprising:

a. topically administering a nonaqueous composition to a subject, wherein the composition comprises:
1) at least one active ingredient;
2) at least one emulsifier;
3) at least one nonaqueous solvent; and
4) at least one thickener;

wherein the active ingredient comprises a polydimethylsiloxane, the composition is non-Newtonian and essentially nonaqueous, and wherein a majority of the ectoparasites are killed after administration of the nonaqueous composition and retention thereof on the treated area for thirty minutes, preferably twenty minutes, and most preferably ten minutes following administration.

In an additional aspect, a kit for killing ectoparasites on a subject is disclosed, the kit including:

a. a nonaqueous composition for the control and elimination of ectoparasites; and b. instructions for the use and application of the nonaqueous composition;

wherein the nonaqueous composition comprises:
1) at least one active ingredient;
2) at least one emulsifier; and
3) at least one nonaqueous solvent, or at least one thickener, or at least one nonaqueous solvent and at least one thickener;

wherein the active ingredient comprises a dimethicone.

In yet an additional aspect, a kit for killing ectoparasites on a subject is disclosed, where the kit comprises:

a. a nonaqueous composition for the control and elimination of ectoparasites;

b. a dispenser or applicator means for applying or topically administering the composition to the subject; and c. instructions for the use and application of the nonaqueous composition;

wherein the nonaqueous composition comprises:
1) at least one active ingredient;
2) at least one emulsifier; and
3) at least one nonaqueous solvent, or at least one thickener, or at least one nonaqueous solvent and at least one thickener;

wherein the active ingredient comprises a dimethicone; and wherein a majority of the ectoparasites are killed after administration of the nonaqueous composition and retention thereof on the treated area for thirty minutes, preferably twenty minutes, and most preferably ten minutes following administration.

Interestingly, the nonaqueous insecticidal or antiparasitic compositions presented herein have been found to exhibit exemplary efficacy when used to treat pest infestations of the hair. Moreover the compositions are easily controllable during application, and easy to rinse from hands and hair following treatment. The fact that these non-pharmaceutical formulations can be used to achieve such a high measure of success is particularly noteworthy. Even without the presence of toxicants such as pyrethrin, rapid and complete parasitic kill can be attained. This is especially important when treatment options are being contemplated for use with children or anyone who may exhibit sensitivities to or prefer to abstain from using pharmaceutical preparations or other medicaments. Thus, the nonaqueous silicone-based topical compositions described herein may be used successfully to treat individuals with *Pediculosis, Phthiriosis*, or other surface pest infestation without requiring prescriptions or harsh chemicals. The compositions described herein are thus particularly well suited for use in situations in which access to pharmaceuticals or medicaments is difficult or nonexistent. A more detailed description of the various components that may be used with the topical, nonaqueous polydimethylsiloxanes compositions described and presented herein follows.

Active Ingredient

The active ingredient most typically contemplated for use with the nonaqueous compositions presented herein comprises polydimethylsiloxane. Polydimethylsiloxane or PDMS is often referred to as dimethicone. Dimethicone or PDMS belongs to the class of organosilicon compounds that are commonly referred to as silicones or silicone oils. As described herein, polydimethylsiloxane is presented in a liquid matrix that has rheology characteristics capable of providing controllable delivery during use. The compositions described herein are essentially free of water, yet they rinse away easily after use from both hands and skin. Formulations prepared according to the instant disclosure may be used as hair conditioners or hair detanglers, but are primarily targeted for use as antiparasitic treatments. The instant disclosure also includes methods for use of topical dimethicone compositions to treat ectoparasite infestations on the skin of a subject. These methods have been found to be safe and effective.

The polydimethylsiloxanes suitable for use herein are preferably relatively non-volatile, so that they stay where applied during treatment, rather than evaporate. This distinguishes them from cyclodimethylsiloxanes such as octamethylcyclotetrasiloxane, decamethylcyclopentasiloxane, and dodecamethylcyclohexasiloxane. As will be known to those skilled in the relevant art, the latter three siloxanes are also known as D4, D5, and D6, respectively. These three cyclodimethylsiloxanes are often used as liquid carriers, but they evaporate at relatively low temperatures. Accordingly, certain cyclodimethylsiloxanes have faced regulatory scrutiny, not solely for their relatively low flash points. Preferably, the flash points of the polydimethylsiloxanes used with the compositions and formulations presented herein have flash points above 95° C. (200° F.).

PDMS or polydimethylsiloxanes are a class of polymeric organosilicon compounds that are known for their unusual rheological or flow properties, and for being relatively inert, non-toxic, and non-flammable. See https://en.wikipedia.org/wiki/Polydimethylsiloxane. The structure of polydimethylsiloxane is represented by structure A below:

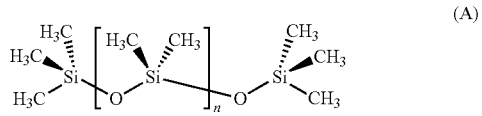

(A)

where n can vary from about 10-1500. As contemplated for use herein, n preferably has a value of 40-1000, and more preferably of 60-500.

As mentioned previously, recent research has shown that neat PDMS is particularly effective at controlling head lice. It is though that PDMS inhibits the ability of a louse to respire and/or to excrete water by externally penetrating their thoracic spiracles. Spiracles are honeycomblike structures that create maximum surface area and efficient exchange of air and moisture. See I. F. Burgess, "The Mode of Action of Dimeticone 4% Lotion Against Head Lice, *Pediculus capitis*," BMC *Pharmacol* 2009 Feb. 20; 9:3. Indeed, in the course of the instant investigations it has been confirmed that if present in pediculocidal preparations, water appears to provide a haven for the parasites until the treatment is removed or eliminated, at which time the parasite continues to live.

There have been numerous products introduced onto the commercial and medical markets, which have taken advantage of this supposed spiracle-blocking phenomena by PDMS. These products are all nonaqueous, either composed entirely of PDMS, or include cyclic dimethylsiloxanes that are volatile and evaporate at room temperature, thus leaving behind non-volatile linear dimethicones.

Low molecular weight polydimethylsiloxanes are Newtonian fluids, meaning that they have constant viscosity as the fluid is subjected to varying amounts of stress. In fact, pure polydimethylsiloxanes are used as standards to calibrate viscometers, precisely because they exhibit Newtonian fluid behavior. Moreover, the viscosity of silicones tends to be relatively constant over a large temperature range. Polydimethylsiloxanes also exhibit very low innate surface tension, meaning that they have little self-cohesion that would inhibit their flow into small orifices, such as the above-mentioned spiracles of head lice. Surface tension is a measure of the stretching force required to form a liquid film, and is equal to the surface energy of the liquid per unit length of the film at equilibrium. The force tends to minimize the area of a surface. Surface tension is caused by the attraction of molecules to each other. The surface tensions of pure polydimethylsiloxanes are approximately 15-25 dynes/cm, most commonly 20-22 dynes/cm, and are surprisingly invariant as a function of molecular weight, despite profound changes in concomitant viscosities. See http://www.clearcoproducts.com/pdf/cosmetic/dimethicones/50-1000cSt.pdf and http://www.clearcoproducts.com/pdf/cosmetic/dimethicones/super-high.pdf. While both Newtonian behavior and low surface tension make PDMS a good choice as a treatment for head lice, they make it difficult to control the flow of a dimethicone product without messy dripping and handling on the hair of a subject during treatment.

Dimethicones presently on the market are available in a wide variety of viscosities, ranging roughly from approximately 0.65 cps to over two million cps. Several neat polydimethylsiloxanes were tested for suitability for use in the formulations presented herein, in order to establish baseline ectoparasite killing efficacy. As cyclic dimethicones are known to be more volatile than non-linear silicones, it was decided to eschew cyclic dimethicones in favor of less volatile linear forms. Not only would this cut down on the wait time for the treatment to be effective, it also eliminates the need to introduce volatile organics into the to ambient atmosphere, thus providing health benefits to the subject, as well as any individuals who might be applying the treatment.

The dimethicones that were selected for initial screening had viscosities ranging from 10 cps to 1000 cps. During the course of evaluation of neat dimethicones, 1-2 drops of sample fluid were dropped onto live lice, which were taken directly from affected patients. The lice were studied over a period of time from five minutes to an hour to assess their ability to survive exposure to the test fluids. Surprisingly, it was found that there was no difference in the number of lice killed at five minutes' exposure as compared to ten minutes, thirty minutes or even longer. The results are shown in Table 1 below.

TABLE 1

EVALUATION OF ACTIVE INGREDIENT

| Sample No. | Active Ingredient (viscosity) | Observed Efficacy[a] |
|---|---|---|
| A1 | Dimethicone (10 cps) | 4 |
| A2 | Dimethicone (350 cps) | 4 |
| A3 | Dimethicone (500 cps) | 4 |

Notes to TABLE 1
[a]Efficacy was evaluated on a scale from 1 to 4 following treatment with the active ingredient as follows:
4 = Elimination of 100% of all live lice within 5 minutes;
3 = Elimination of 75% of live lice within 5 minutes (25% live lice remain);
2 = Elimination of 50% of live lice after 5 minutes (50% live lice remain);
1 = Elimination of 25% of lice after 5 minutes (75% live lice remain); and
0 = No elimination of live lice after 5 minutes (100% live lice remain).

While it was believed from academic literature (see I. F. Burgess, vide infra), patents (see U.S. Pat. No. 8,097,602 to Holzer) and commercial products that dimethicones with viscosities of at least 350-100,000 cps may be needed to be effective, it was surprisingly found during the course of the instant body of work that dimethicones with much lower viscosities were actually quite effective in killing lice. In fact, even after waiting for longer periods of time to ensure that the lice were truly deceased and not stunned or in some suspended state, it was found that the number of lice that appeared to have been killed after ten or even five minutes' time remained constant. There appeared to be no difference in the number of lice killed at five minutes' exposure as compared to ten minutes, thirty minutes or even longer from the time of application.

The polydimethylsiloxanes represented in structure A above contain terminal trimethylsiloxy groups, and as such are preferred for their ready availability, favorable antiparasitic properties and chemical inertness. It is however also foreseen that compounds with substitutions of the terminal methyl groups may be useful singly or in combination with compounds according to structure A, provided that they do not interfere with the antiparasitic efficacy, rheology, or rinsibility of the formulations in which they are used.

In the course of evaluating different dimethicones for use in the compositions presented herein, it was determined that there is an overall preferred range of viscosities for the dimethicones that are contemplated for use herein. Thus, dimethicones having a viscosity from about 10 cps to about 100,000 cps are acceptable for use herein, preferably those with viscosities from about 100 cps to about 10,000 cps, more preferably from about 350 cps to about 5,000 cps, and most preferably from about 500 cps to about 1,000 cps.

The amount of active ingredient that may be used with the nonaqueous compositions of the instant disclosure ranges from about 5.0 wt. % to about 100.0 wt. %. A preferred range for the amount of active ingredient is from about 10.0 wt. % to about 95.0 wt. %, and a more preferred range is from about 10.0 wt. % to about 90 wt. % of the total composition. When the active ingredient is dimethicone, a suitable quantity for use with the formulations presented herein is from about 15.0 wt. % to about 95.0 wt. %, more preferably from about 20 wt. % to about 85 wt. %, and most preferably from about 25.0 wt. % to about 75.0 wt. % of the total formulation. Individual siloxanes as well as mixtures of various siloxanes may be used with the compositions described and presented herein.

Sources for dimethicones are numerous, among which include those sold under the Andisil® trade name available from AB Specialty Silicones, Waukegan, Ill.; the Xiameter® trade name available from Dow Corning Corporation, Midland, Mich.; SF fluids available from Momentive Performance Materials, Waterford, N.Y., and the Belsil® trade name available from Wacker Chemical Corporation, Adrian, Mich.).

Emulsifier

As indicated previously, dimethicones or polydimethylsiloxanes (PDMS) are desired active ingredients for use in ectoparasite treatments according to a number of embodiments of the compositions presented and described herein. Upon completion of treating a subject with a dimethicone-containing composition, it is desirable to easily and conveniently wash away the active ingredient from the subject, without having to resort to the use of additional products. Unfortunately, dimethicones are known to have very low water solubility, making their removal from a treated subject and implements used to treat a subject after use both difficult and very often messy.

PDMS can be emulsified or suspended within an aqueous matrix by use of silicone-based emulsifiers and/or polymers that rely on water for their thickening ability. Compositions that are formed by combining siloxanes with emulsifiers such as surfactants in the presence of water are known to generally form gel-type matrices with regions of water suspended within the matrix. However, we have confirmed during the course of the instant work that—when present in products such as conditioners and shampoos that are formulated from siloxanes and surfactants—water significantly diminishes the effectiveness of the dimethicone in killing ectoparasites, especially lice. Without being bound by theory, one explanation that has been proposed for this phenomenon is that lice are sensitive to the presence of water. Stated another way, lice seem to be able to physiologically detect the presence of water. When they significant quantities of water are detected in which they might otherwise drown, it appears that they are capable of going into a mode of suspension, whereby they can survive for extended periods of time.

Prior to the instant disclosure, there have been relatively few nonaqueous PDMS-based products that were available for topical use in treating infestations of ectoparasites. More particularly, there have not been nonaqueous, PDMS-based mixtures that exhibit good risibility while still demonstrating desirable efficacy in the killing of lice, nits and other insects such as fleas and ticks. Surprisingly, however, it has now been found that it is possible to formulate rinsable, nonaqueous preparations for efficacious use in treating ectoparasite infestations that offer distinct advantages over a number of prior art products. More particularly, small amounts of an emulsifier have been found to be effective for use with the compositions described herein in order to assist in the solubilization and ultimately removal of the compositions after use. It has now been found that many surfactants can be formulated into rinsable, nonaqueous compositions, they can successfully be used as emulsifiers with the formulations of the instant disclosure, and they can be effective against ectoparasites when incorporated in an anhydrous form.

In general, surfactants that are anionic, cationic, nonionic, amphoteric—also called zwitterionic—as well as combinations of any of the foregoing, may be used as emulsifiers with the compositions described herein. One criterion for selecting a suitable surfactant is that it should not contain any water as it is obtained from the manufacturer, such that it is delivered as a nonaqueous active. If a surfactant is found to contain some water, it may be made acceptable for use with the compositions presented herein, provided that the water can be and is removed prior to formulation. As discussed previously, the presence of even small amounts of water can be deleterious to the insecticidal efficacy of the composition presented herein. Also, it is advantageous for the surfactant or surfactants to be fluid at room temperature, at least when combined with the active ingredients and solvent. Nonionic surfactants are therefore preferred for use over surfactants such as anionic, cationic, and amphoteric surfactants, which may significantly raise the viscosity of the product to where it is no longer flow able or result in a non-liquid product state.

Numerous nonionic surfactants that are suitable for use in the instant disclosure include addition products of fatty alcohols, fatty acids, and fatty amines (sourced from bio-based materials such as vegetable oils or animal fats, or from petroleum or natural gas derivatives), coupled with alkoxylating agents such as ethylene oxide (EO), propylene oxide (PO), isopropylene oxide (IPO), or butylene oxide (BO), or a mixture thereof. Any of the alkoxylated materials of the particular type described hereinafter can be used as the nonionic surfactant. Preferably, the nonionic surfactant is selected from the group consisting of primary and secondary alcohol ethoxylates as well as mixtures thereof. Nonionic surfactants may also contain a mixture of alcohol ethoxylates and propoxylates and mixtures thereof. Further examples of suitable surfactants are described in McCutcheon's Vol. 1: Emulsifiers and Detergents, North American Ed., McCutcheon Division, MC Publishing Co., 1995, which is incorporated herein by reference.

Highly preferred nonionic surfactants for use with the topical, non-Newtonian compositions of the instant disclosure include alcohol ethoxylates, represented by the general structure: $R(OCH_2CH_2)_nOH$, where R can be $C_6$-$C_{18}$, and n can be from 1-15. Also highly preferred nonionic surfactants for use with the topical, non-Newtonian compositions of the instant disclosure include alcohol alkoxylates, represented by the general structure: $R(OCH_2-CH_2)_m(OCH(CH_3)CH_2)_nOH$, where R can be $C_6$-$C_{18}$, m can be from 1-15, and n can be from 1-15. Many different alcohol ethoxylates are contemplated for use with the compositions and methods of the instant disclosure. Suitable alcohol alkoxylates that may be used are those containing from five to twenty-five carbon atoms ($C_5$-$C_{25}$) with from five to twenty-five ethylene oxide units (5-25 EO) and from zero to twenty-five propylene oxide units (0-25 PO). More preferable are $C_7$-$C_{25}$ alcohol ethoxylates having seven to twenty-five ethylene oxide units (7-25 EO). Individual nonionic surfactants as well as mixtures of nonionic surfactants may be used with the compositions described and presented herein.

Other surfactants envisioned for use with the topical, non-Newtonian compositions of the instant disclosure may also include but are not limited to anhydrous sources of other nonionic surfactants (for example, glycosides, amides, and esters); anionic surfactants (for example, sodium alkylbenzene sulfonate, sodium alkyl sulfate, or sodium alpha-olefin sulfonate); cationic surfactants (for example, quaternary ammonium or phosphonium salts); and amphoteric surfactants (for example, amine oxides, betaines, sultaines, imidazoline derivatives such as glycinates and propionates, lecithins, or amino propionic acids). Further examples of suitable surfactants are described in McCutcheon's Vol. 1: Emulsifiers and Detergents, North American Ed., McCutcheon Division, MC Publishing Co., 1995, which is incorporated herein by reference.

The amount of surfactant emulsifier that is suitable for use with the nonaqueous compositions presented herein can be anywhere from about 0.1 wt. % to about 50 wt. %, preferably from about 0.5 wt. % to about 35 wt. %, and more preferably from about 1.0 wt. % to about 25 wt. %. When the surfactant is a nonionic alcohol ethoxylate, the amount of surfactant suitable for use with the nonaqueous compositions described herein is preferably from about 1.0 wt. % to about 25 wt. % of the total composition.

There are numerous sources of suitable nonionic surfactants; the following in no way is meant to restrict acceptable sources thereof. Suitable examples of nonionic surfactants include primary alcohol ethoxylates include those under the Bio-Soft® trade name (Stepan Company, particularly the Bio-Soft N-series, such as $C_{9-11}$ alcohol condensed with 2.5 moles of ethylene oxide (Bio-Soft N91-2.5), $C_{9-11}$ alcohol condensed with 6 moles of ethylene oxide (Bio-Soft N91-6), $C_{9-11}$ alcohol condensed with 8 moles of ethylene oxide (Bio-Soft N91-8), $C_{11}$ alcohol condensed with 3 moles of ethylene oxide (Bio-Soft N1-3), $C_{11}$ alcohol condensed with 5 moles of ethylene oxide (Bio-Soft N1-5), $C_{11}$ alcohol condensed with 7 moles of ethylene oxide (Bio-Soft N1-7), $C_{11}$ alcohol condensed with 9 moles of ethylene oxide (Bio-Soft N1-9), $C_{12-13}$ alcohol condensed with 3 moles of ethylene oxide (Bio-Soft N23-3), $C_{12-13}$ alcohol condensed with 6.5 moles of ethylene oxide (Bio-Soft N23-6.5), $C_{12-15}$ alcohol condensed with 3 moles of ethylene oxide (Bio-Soft N25-3), $C_{12-15}$ alcohol condensed with 7 moles of ethylene oxide (Bio-Soft N25-7), and $C_{12-15}$ alcohol condensed with 9 moles of ethylene oxide (Bio-Soft N25-9). Other examples of nonionic surfactants available from Stepan Company include $C_{11-13}$ alcohol condensed with 7 moles of ethylene oxide (Bio-Soft EC-600 and Bio-Soft EC-690) and $C_{11-13}$ alcohol condensed with 8.2 moles of ethylene oxide (Bio-Soft EC-639).

Other examples of nonionic surfactants suitable for use in the present invention include those available under the Neodol® trade name (Shell Co., Houston, Tex.), such as $C_{11}$ alcohol condensed with 9 moles of ethylene oxide (Neodol 1-9), $C_{12-13}$ alcohol condensed with 6.5 moles of ethylene oxide (Neodol 23-6.5), $C_{12-13}$ alcohol with moles of ethylene oxide (Neodol 23-9), $C_{12-15}$ alcohol condensed with 7 moles of ethylene oxide (Neodol 25-7), $C_{14-15}$ alcohol condensed with 13 moles of ethylene oxide (Neodol 45-13), $C_{9-11}$ linear ethoxylated alcohol, averaging 2.5 moles of ethylene oxide per mole of alcohol (Neodol 91-2.5), and the like.

Other examples of nonionic surfactants suitable for use in the present invention include ethylene oxide condensate products of secondary aliphatic alcohols containing 11 to 18 carbon atoms in a straight or branched chain configuration condensed with 5 to 30 moles of ethylene oxide (such as those marketed under the Tergitol® trade name from Dow Chemical, Midland, Mich.). Examples of commercially available non-ionic detergents of the foregoing type are $C_{11-15}$ secondary alcohol condensed with either 9 moles of ethylene oxide (Tergitol 15-S-9) or 12 moles of ethylene oxide (Tergitol 15-S-12).

Other examples of linear primary alcohol ethoxylates are available under the Tomadol® trade name (manufactured by Air Products and Chemicals Inc., Allentown, Pa.) such as Tomadol 1-7, a $C_{11}$ linear primary alcohol ethoxylate with 7 moles of ethylene oxide; Tomadol 25-7, a $C_{12}$-$C_{15}$ linear primary alcohol ethoxylate with 7 moles of ethylene oxide; Tomadol 45-7, a $C_{14}$-$C_{15}$ linear primary alcohol ethoxylate with 7 moles of ethylene oxide; and Tomadol 91-6, a $C_9$-$C_{11}$ linear alcohol ethoxylate with 6 moles of ethylene oxide.

Other examples of linear primary alcohol ethoxylates are available under the Lutensol® trade name (BASF Corporation, Florham Park, N.J.) such as, for example, Lutensol A3N, a $C_{13-15}$ linear primary alcohol ethoxylate with 3 moles of ethylene oxide; Lutensol LA60, a $C_{13-15}$ linear primary alcohol ethoxylate with 7 moles of ethylene oxide. Also acceptable are alcohol ethoxylates available under the Genapol® trade name (Clariant, Charlotte, N.C.) such as, for example, Genapol LA3, a $C_{13-15}$ linear primary alcohol ethoxylate with 3 moles of ethylene oxide; Genapol LA070, a $C_{13-15}$ linear primary alcohol ethoxylate with 7 moles of ethylene oxide.

Thickener

Numerous types of thickeners are commercially available that can be foreseen as rendering non-Newtonian rheology, preferably shear-thinning properties in particular, to liquid compositions. In reality, however, the majority of these are activated only in the presence of water: as we have determined in our laboratories, the presence of any significant amount of water in our compositions significantly reduced the effectiveness of the desired ectoparasiticidal effects. Certain thickeners appear to render non-Newtonian rheological properties in the absence of significant levels of water in the compositions. Without being limited by theory, we believe this may be due to space-filling characteristics of the thickeners, for example localized areas of solid or semi-solid phases dispersed within the liquid composition. The presence of such solids or semi-solids inhibits free flow ability until the composition is forced to move through external stress.

Preferred thickeners are those that render thickening without requiring the addition of water. Prior to the current work, it was well established that ester-, amide- and/or ether-terminated polyamides were not regarded as being compatible with compositions containing polydimethylsiloxanes. However, during the course of the work presented herein, it was surprisingly found that certain polymers, including ester-, amide- and/or ether-terminated polyamides, are in fact able to render thickening to anhydrous compositions when combined with the components and in the manner described herein. Accordingly, thickeners that are preferred fix use with the nonaqueous, non-Newtonian compositions described herein are those that are capable of providing thickening characteristics in. an anhydrous environment. A number of polyamides, such as those terminating in ester, amide and/or ether groups have been found to satisfy this criteria. Representative structures for ester-, amide- and ether-terminated polyamides are provided at B, C and D, respectively:

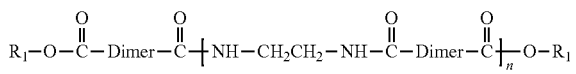

An ester-terminated polyimide, where $R_1$ is a fatty alkyl chain;

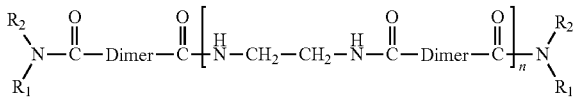

An amide-terminated polyamide, where $R_1$ is a methyl group and $R_2$ is an ethyl or propyl residue; and

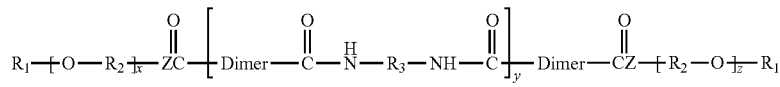

An ether-terminated polyamide, where $R_1$ is a methyl group and $R_2$ is an ethyl or propyl residue.

Thus, formulating must be carried out in such a manner as to provide non-Newtonian rheology to the compositions of the instant disclosure, while still generating a stable mixture. Also acceptable for use as thickeners herein are silica-based compounds, an example of which is as fumed silica, clay-based compounds such as bentonite, as well as other minerals, an example of which is magnesium aluminum silicate.

It has been found that even small quantities of thickeners can be beneficial for use with the nonaqueous ectoparasite treatment compositions presented herein. In general, thickeners in amounts of from about 0.1 wt. % to about 30 wt. %, preferably from about 0.2 wt. % to about 25.0 wt. % and more preferably thickeners from about 0.5 wt. % to about 20 wt. % of the total composition may be used according to several embodiments of the compositions and methods presented herein. Depending on the nature of the thickener contemplated for use with the compositions presented herein, lower levels of thickener may be used. Thus, for example, in alternate embodiments where thickeners comprise ester- or amide-terminated polyamides, the amount of thickener can vary from about 0.1 wt. % to 20 wt. %, preferably from about 0.5 wt. % to about 15 wt. %, and more preferably from about 1.0 wt. % to about 10 wt. % of the total composition. According to yet additional embodiments, when the compositions presented herein comprise polyamide thickeners, the amount of thickener can vary from about 0.1 wt. % to 20 wt. %, preferably from about 0.5 wt. % to about 18 wt. %, and more preferably from about 1.0 wt. % to about 15 wt. % of the total composition.

Polyamide thickeners are available from numerous sources, a representative sampling including but not limited to those under the CrystaSense® trade name (Croda Incorporated, Hollywood, Fla.), under the Sartomer® and Crayvallac® trade names (Arkema Incorporated, King of Prussia, Pa.), under the Disparlon® trade name (King Industries, Inc., Norwalk, Conn.), and under the Rheothix™ trade name (KeumJung Company, Ltd., South Korea). Especially preferred are ester-terminated polyamides such as CrystaSense LP-1 and CrystaSense LP-2, as well as amide-terminated polyamides such as CrystaSense LP-3 (all from Croda Incorporated).

Certain inorganic thickeners have also been noted as useful in our inventive compositions, including but not limited to silica-based compounds (such as fumed silica), clay-based compounds (such as bentonite), or other minerals (such as magnesium aluminum silicate). Representative sources of fumed silicas include, but are not limited to, those under the Aerosil® trade name (Evonik Industries, Piscataway, N.J.), under the Cab-O-Sil® trade name (Cabot Corporation, Alpharetta, Ga.), under the Accelguard® trade name (Euclid Chemical Company, Cleveland, Ohio), and under the Microsilica® trade name (Elkem Material, Incorporated, Pittsburgh, Pa.). Especially preferred fumed silica is Aerosil 200 (Evonik Industries). Representative sources of bentonite include, but are not limited to, those under the Bentobrite® trade name (American Colloid Corporation, Hoffman Estates, Ill.), under the Hydrogel® trade name (Wyo-Ben, Incorporated, Billings, Mont.), under the SwellGel™ trade name (Redmond Minerals, Incorporated, Heber City, Utah), and under the PermaPlug® trade name (Teague Mineral Products, Adrian, Oreg.). Representative sources of magnesium aluminum silicate include but are not limited to those under the Veegum® trade name (Vanderbilt Minerals, LLC, Norwalk, Conn.), under the Acti-Gel® trade name (Active Materials International, LLC, Hunt Valley, Md.), under the Magnabrite® trade name (AMCOL Health & Beauty Solution, Hoffman Estates, Ill.) and under the Optigel® trade name (Eckart America, Painesville, Ohio).

Solvent

According to one embodiment, the compositions of the instant disclosure comprise an active ingredient, an emulsifier and a thickener, as discussed above. In an alternate embodiment, the compositions of the instant disclosure comprise an active ingredient, an emulsifier and a solvent. In yet alternate embodiments, the compositions of the instant disclosure comprise, in addition to an active ingredient and an emulsifier, both a solvent and a thickener.

Solvents that are suitable for use with the nonaqueous compositions described herein may be selected from among polar, semi-polar and non-polar classes of solvents, as well as mixtures of any of the foregoing. Preferred solvents explicitly do not include water or mixtures with water, as water has been found to decrease or eliminate the effectiveness of the formulations. As such, the total water level in the composition should less than 5%, more preferably less than 2%, and most preferably less than 0.5%. Especially preferred is for water to be totally absent.

Examples of polar solvents include alcohols, polyols, amines, and mixtures of any of the foregoing. Examples of semi-polar solvents include esters, amides and mixtures of any of the foregoing. Examples of non-polar solvents include hydrocarbons, as well as any mixtures thereof. Mixtures of combinations of one or more of any polar, semi-polar and non-polar solvents are also contemplated and may be formulated for use with the compositions described and presented herein. In order to be as compatible as possible with the active ingredient, it is preferred that the solvent not be very polar, that is at least semi-polar if not polar. Measurement of the polarity of a solvent is reflected in its dielectric constant (δ). Preferred solvents would have dielectric constants below 80, more preferred solvents would have dielectric constants below 40, yet more preferred solvents would have dielectric constants below 20, and most preferred solvents would have dielectric constants below 10. Solvents that are suitable for use with the compositions described herein include one or more ingredients selected from among $C_1$-$C_6$ alkanols, $C_1$-$C_6$ diols, $C_1$-$C_{10}$ alkyl ethers of alkylene glycols, $C_3$-$C_{24}$ alkylene glycol ethers, polyalkylene glycols, short chain carboxylic acids, short chain esters, isoparaffinic hydrocarbons, mineral spirits, alkylaromatics, terpenes, terpene derivatives, terpenoids, terpenoid derivatives, formaldehyde, and pyrrolidones, as well as combinations of any of the foregoing. Butyl 3-hydroxybutyrate and isopropyl myristate are both preferred for use herein, as well as combinations of the foregoing. One especially preferred solvent is isopropyl myristate, which has a dielectric constant of 3.2.

According to several embodiments presented herein, it has been found that relatively non-polar solvents are preferred for use in generating effective ectoparasite treatment compositions. Among non-polar solvents, butyrates, myristates and glycols have been found to provide compositions with desirable characteristics as well as and performance results. Combinations of any of the foregoing may also be used. Isobutyl butyrates, isopropyl myristates and propylene glycols are preferred butyrates, myristates and glycols, respectively. In particular, different embodiments in which butyl-3-hydroxybutyrate, isopropyl myristate and propylene glycol were used have each been found to provide desirable formulations with respect to convenience in handling and applying the treatment, effectiveness in killing numbers of infecting insects, and ease of cleaning up and rinsing away the composition upon completion of the treatment.

When used, the amount of solvent that is appropriate for use in formulating the nonaqueous compositions presented herein ranges from about 1.0 wt. % to about 60 wt. %, more preferably from about 5 wt. % to about 55.0 wt. %, and most preferably from about 10.0 wt. % to about 50 wt. %. Solvents are available from numerous sources, a representative sampling of which include BASF Corporation, Croda Incorporated, Dow Chemical, Eastman Chemical Company, LyondellBasell Industries, Specialty Materials Company, and the like. Especially preferred solvents include isopropyl myristate from Croda Incorporated from Hollywood, Fla., BASF Corporation from Florham Park, N.J., Omnia™—for butyl-3-hydroxybutyrate—from Eastman Chemical Company in Kingsport, Tenn., and propylene glycol from Dow Chemical, in Midland, Mich.

Fragrance

Perfumes or fragrance materials may be added to the composition. The selection of the perfume or perfumes maybe based upon the application, the desired effect on the consumer, and preferences of the formulator. The perfume selected for use in the compositions and formulations of the present invention may contain ingredients with odor characteristics which are preferred in order to provide a fresh impression on the surface to which the composition is directed, for example, those which provide a fresh impression for fabrics. Such perfume may be preferably present at a level from about 0.01 wt. % to about 5 wt. %, preferably from about 0.05 wt. % to about 3 wt. %, and more preferably from about 0.1 wt. % to about 2 wt. % of the total composition.

Preferably, the perfume may be composed of fragrance materials selected from the group consisting of aromatic and aliphatic esters having molecular weights from about 130 to about 250; aliphatic and aromatic alcohols having molecular weights from about 90 to about 240; aliphatic ketones having molecular weights from about 150 to about 260; aromatic ketones having molecular weights from about 150 to about 270; aromatic and aliphatic lactones having molecular weights from about 130 to about 290; aliphatic aldehydes having molecular weights from about 140 to about 200; aromatic aldehydes having molecular weights from about 90 to about 230; aliphatic and aromatic ethers having molecular weights from about 150 to about 270; and condensation products of aldehydes and amines having molecular weights from about 180 to about 320; and mixtures thereof. Examples of such perfumes or fragrance materials include, but are not limited to: adoxal (2,6,10-trimethyl-9-undecen-1-al), allyl amyl glycolate, allyl cyclohexane (allyl-3-cyclohexylpropionate), amyl acetate (3-methyl-1-butanol), amyl salicylate, anisic aldehyde (4-methoxybenzaldehyde), aurantiol (condensation product of methyl anthranilate and hydroxycitronellal), bacdanol (2-ethyl-4-(2,2,3-trimethyl-3-cyclopenten-1-yl)-2-buten-1-ol), benzaldehyde, benzophenone, benzyl acetate, benzyl salicylate, damascone (1-(2,6,6-trimethyl-1-cyclohexen-1-yl)-2-buten-1-one, 3-hexen-1-ol, buccoxime (1,5-dimethyl-oximebicyclo[3,2,1]octan-8-one), cedrol (octahydro-3,6,8,8-tetramethyl-1H-3A,-7-methanoazulen-6-ol), cetalox (dodecahydro-3A,6,-6,9A-tetramethylnaphtho[2,1]furan), cis-3-hexenyl acetate, cis-3-hexenyl salicylate, citronellol (3,7-dimethyl-6-octenol), citronellyl nitrile (geranyl nitrile), clove stem oil, coumarin, cyclohexyl salicylate, cymal (2-methyl-3-(p-isopropyl-phenyl)-propionaldehyde), decyl aldehyde, damascone (1-(2,6,6-trimethyl-3-cyclohexen-1-yl)-2-buten-1-one), dihydromyrcenol (2,6-dimethyl-7-octan-2-ol), dimethyl benzyl carbinyl acetate, ethyl vanillin, ethyl-2-methyl butyrate, ethylene brassylate (ethylene tridecan-1,13-dioate), eucalyptol (1,8-epoxy-p-menthane), eugenol (4-allyl-2-methoxyphenol), exaltolide (cyclopentadecanolide), flor acetate (dihydronorcyclopentadienyl acetate), florhydral (3-(3-isopropylphenyl)butanal), frutene (dihydronorcyclopentadienyl propionate), galaxolide (1,3,4,6,7,8-hexahydro-4,6,6,7,8,8-hexamethylcyclopent-gamma-2-benzopyrane), gamma-decalactone (4-N-heptyl-4-hydroxyaldehyde), cinnamic aldehyde, hexyl salicylate, hydroxyambran (2-cyclododecylpropanol), hydroxycitronellal, ionone (4-(2,6,6-trimethyl-1-cyclohexenyl-1-yl)-3-buten-2-one), ionone (4-(2,6,6-trimethyl-1-cyclohexene-1-yl)-3-butene-2-one), ionone (4-(2,6,6-trimethyl-2-methylcyclohexyl-1-yl)-3-methyl-3-buten-2-one), 7-acetyl-1,2,3,4,5,6,7,8-octahydro-1,1,6,7-tetramethylnaphthalene, isoeugenol (2-methoxy-4-(1-propenyl)-phenol), isojasmone (2-methyl-3-(2-pentenyl)-2-cyclopenten-1-one), koavone (acetyl di-isoamylene), lauric aldehyde, lavandin, lavender, natural lemon (major component d-limonene), d-limonene/orange terpenes (1-methyl-4-isopropenyl-1-cyclohexene), linalool (3-hydroxy-3,7-dimethyl-1,6-octadiene), linalyl acetate (3-hydroxy-3,7-dimethyl-1,6-octadiene acetate), Irg™ 201 (2,4-dihydroxy-3,6-dimethyl benzoic acid methyl ester), lyral (4-(4-hydroxy-4methyl-pentyl)-3-cyclohexene-1-carboxaldehyde), majantol (2,2-dimethyl-3-(3-methylphenyl)-propanol), mayol (4-(1-methylethyl)-cyclohexanemethanol), methyl anthranilate (methyl-2-aminobenzoate), methyl-alpha-naphthyl ketone, methyl cedrylone (methyl cedrenyl ketone), methyl chavicol (1-methyloxy-4,2-propen-1-yl benzene), methyl dihydrojasmonate, methyl nonyl acetaldehyde, musk indanone (4-acetyl-6-tert-butyl-1,1-dimethylindane), nerol (2-cis-3,7-dimethyl-2,6-octadien-1-ol), nonalactone (4-hydroxynonanoic acid lactone), norlimbanol (1-(2,2,6-trimethyl-cyclohexyl)-3-hexanol), orange CP (major component d-limonene), para-tert-bucinal (2-methyl-3-(p-tert-butylphenyl)-propionaldehyde), p-hydroxyphenylbutanone, patchouli, phenyl acetaldehyde (1-oxo-2-phenylethane), phenyl acetaldehyde, dimethyl acetal, phenyl ethyl acetate, p-menth-1-en-8-ol, p-menth-1-en-1-ol, terpinyl acetate p-menth-1-en-8-yl acetate), tetrahydrolinalool (3,7-dimethyl-3-octanol), tetrahydromyrcenol (2,6-dimethyl-2-octanol), tonalid/musk plus (7-acetyl-1,1,3,4,4,6-hexamethyltetralin), undecalactone (4-N-heptyl-4-hydroxybutanoic acid lactone), undecavertol (4-methyl-3-decen-5-ol), undecanal, undecylenic aldehyde, vanillin (4-hydroxy-3-methoxybenzaldehyde), verdox (2-tert-butyl cyclohexyl acetate), vertenex (4-tert-butyl cyclohexyl acetate), and mixtures thereof.

The selection of such perfumes and fragrance materials is well-known to those of skill in the art, both for desired scent and appropriate scent impact. For example, when high residual perfume odor impact following use is desired, it can be preferable to select a perfume containing perfume ingredients that is relatively hydrophobic. The degree of hydrophobicity of a perfume ingredient can be correlated with its octanol/water partitioning coefficient P, the ratio between its equilibrium concentration in octanol and in water. Thus, a perfume ingredient with a greater partitioning coefficient P is more hydrophobic and a perfume ingredient with a smaller partitioning coefficient P is more hydrophilic; a selection based on the application and intended effect may be made accordingly. For example, in a fabric application, the preferred perfume ingredients may have an octanol/water partitioning coefficient P of about 1,000 or smaller.

Highly preferred materials of this class of fragrances and perfumes are those that do not cause any significant color change, nor impart any discoloration, such as graying or yellowing, to the subjects to which they are applied.

Fragrance manufacturers and suppliers are numerous, and include without restriction Berjé Incorporated (Carteret, N.J.), Custom Essence, Incorporated (Somerset, N.J.), Firmenich Incorporated (Princeton, N.J.), International Fragrance and Flavors, Incorporated (New York City, N.Y.), and Symrise Incorporated (Teterboro, N.J.).

Colorant

Colorants can be optionally added to the compositions of the present invention for visual appeal and performance impression. When colorants are used, they may be used at extremely low levels to avoid staining of individuals' hands, hair, and the like. Preferred colorants for use in the present compositions do not bring added water into the formulation. For example, pigments and so-called lakes may be especially preferred for this purpose.

Pigments are colorants that are insoluble in water and oil, and impart color to compositions in which they are suspended. They are obtained in a solid state or suspended in a pre-mixed liquid matrix. Pigments are differentiated from dyes, the latter of which are either water- or oil-soluble, and are thus delivered as a readily soluble powder or in a pre-dissolved liquid matrix. Pigments can be obtained through natural sources, for example chlorophyll, the green coloring matter of leaves responsible for photosynthesis; heme, which gives blood its red color); and ultramarine blue, which was originally made by grinding lapis lazuli into a powder. Insoluble transition metal-based mineral compounds are an abundant source of natural pigments. Pigments can also be synthetic, such as phthalocyanines, which can be manmade coordination complexes, often derived from said transition metals. A subgroup of pigments is so-called lake pigments, in which an organic dye is deposited on an insoluble particle, termed a mordent. The most common support particle used is alumina; their resulting colorant is called an "aluminum lake." In essence, it is foreseen that any water- or oil-soluble dye can be turned into a lake pigment.

Suitable colors include, but are not limited to pigments or lake pigments derived from Acid Black 1, Acid Blue 3, Acid Blue 9, Acid Blue 74, Acid Green 1, Acid Orange 6, Acid Red 14 Aluminum Lake, Acid Red 27, Acid Red 51, Acid Violet 9, Acid Yellow 3, Acid Yellow 73, Aluminum Powder, Basic Blue 6, Basic Yellow 11, Carotene, Brilliant Black 1, Bromocresol Green, Chromium Oxide Greens, Curry Red, D&C Blue No. 1 Aluminum Lake, D&C Blue No. 4, D&C Brown No. 1, D&C Green No. 3, D&C Green No. 5, D&C Orange No. 4, D&C Red No. 6, D&C Red No. 6, D&C Violet No. 2, D&C Yellow No. 7, D&C Yellow No. 10, D&C Yellow No. 11, D&C Blue No. 1, FD&C Yellow No. 5, iron oxides, Pigment Orange 5, Pigment Red 83, Pigment Yellow 73, Solvent Orange 1, Solvent Yellow 18, ultramarines, and zinc stearate. Especially preferred are lakes prepared from FD&C Blue No. 1, FD&C Yellow No. 5, and mixtures thereof.

It is also foreseen that lake pigments may be prepared from commercial water-soluble dyes, for example, LIQUITINT dyes available from Milliken Chemical Company. Non-limiting examples of suitable dyes that can be used in preparing lakes are LIQUITINT Blue HP, LIQUITINT Blue 65, LIQUITINT Patent Blue, LIQUITINT Royal Blue, LIQUITINT Experimental Yellow 8949-43, LIQUITINT Green HMC, LIQUITINT Yellow II, and mixtures thereof.

Typical concentrations of these compounds may range from about 0.001 wt. % to about 0.8 wt. %, preferably from about 0.005 wt. % to about 0.3 wt. %, and more preferably from about 0.01 wt. % to 0.2 wt. % of the usage composition.

Colorant manufacturers and suppliers are numerous, and include without restriction IFC Solutions (Linden, N.J.), Milliken (Spartanburg, S.C.), Emerald Hilton Davis (Cincinnati, Ohio), and Chromatech Incorporated (Canton, Mich.).

Additional Ingredients

As will be readily understood by those skilled in the relevant art, additional ingredients may also be used with the compositions disclosed herein, as desired. Such additional ingredients include, but are not necessarily limited to, antibacterial agents, antidandruff agents, foam boosters, preservatives, proteins, buffering or pH adjusting agents, moisturizing agents, vitamins, herb or other plant extracts and other natural ingredients, as well as combinations of any of the foregoing.

Rheology

The inherent surface tensions of the active ingredient, emulsifier, and solvent—taken individually and collectively—are such that the compositions readily not only flow, but also spontaneously spread with little resistance. Indeed, polydimethylsiloxane fluids have a very low surface tension and because of this they are good wetting agents and show good spreadability properties (see https://www.dowcorning.com/content/publishedlit/27-1253-01.pdf). The liquid surface tension of polydimethylsiloxane (21 dynes/cm) is lower than the critical surface tension of wetting (24 dynes/cm). This causes the polymers to spread over their own adsorbed films. The ability of silicone to promote spreading also depends on its compatibility with other components from the formulation.

While the low surface tension can be advantageous, for example, in aiding the penetration of the compositions into the small-scale spiracles of the head lice, it also causes the composition to be difficult to control, even with dispensing devices such those described herein. Consequently, it is advantageous to cause thicken the composition by incorporation of thickening agents described above. Especially preferred are agents that can effect non-Newtonian rheology in the composition, such that composition readily flows in the presence of applied stress (for example, squeezing of the dispensing means), yet will cease to flow in the absence of the applied stress. Such especially preferred compositions exhibit so-called pseudoplastic behavior, and most preferably are so-called Bingham plastics.

Non-Newtonian behavior can be quantified by measuring the viscosity of liquids at different shear rates: shear-thinning liquids have lower apparent viscosity at higher shear rates, while shear-thickening liquids have higher apparent viscosity at higher shear rates. Thixotropic liquids exhibit time-dependent shear thinning property, that is, they are viscous under static conditions, but will flow over time when shaken, agitated, or otherwise stressed. See https://en.wikipedia.org/-wiki/Thixotropy. Some thixotropic fluids return to a gel state almost instantly, such as ketchup, and are called pseudoplastic fluids. This behavior is especially preferred for controlled delivery of compositions through a dispensing means described herein. Less preferred behavior are those liquids that exhibit Newtonian behavior, that is, wherein viscosity is constant independent of shear stress. Such liquids flow without shaking, agitation, squeezing, or otherwise. Such fluids will readily flow uncontrollable through a dispensing means described herein. Least preferred liquids are those that thicken as shear stress is applied; such liquids are called dilatant, and can such liquids can be extremely difficult to deliver through a dispensing means described herein.

While the type and amount of thickener must be sufficient to provide non-Newtonian rheology to the composition, it must be done so with the reference point of being able to deliver the composition through a dispensing means to the treatment site. If the choice of thickener or amount thereof is such that the composition is too viscous to initiate flow of the composition through the orifice or orifices of the dispensing device, it will become too burdensome to deliver the composition to the treatment site. Depending to some extent on the gender of the individual, the maximum force that the human hand can grip is approximately 140 pounds, with the average being between 57-113 pounds, and poor grip strength varying between 44 and 88 pounds. See http://www.topendsports.com/testing/tests/handgrip.htm. It is foreseen that no more than 40 pounds of force should be needed to initiate flow of the composition through the orifice or orifices of the dispensing device.

Qualitative determination of non-Newtonian rheology can be demonstrated through a Zahn cup test, as well as through a tilt drop test. In a Zahn cup test, a small hole is drilled in the center of the bottom of the cup, to which a long handle attached. The cup is dipped and completely filled with the substance to be tested: after lifting the cup out of the substance the user measures the time until the liquid streaming out of it breaks up, this is the corresponding "efflux time" (see https://en.wikipedia.org/wiki/Zahn_cup). Shorter efflux times can indicate that the viscosity is rising in the absence of shear stress, characteristic of a pseudoplastic liquid. In a tilt drop test, a volume of liquid is dropped to a level surface, and its diameter is measured. The surface is then slowly inclined, for example to 20°, and the drop size is measured again after a defined time, for example one minute. Liquids with significant pseudoplasticity will have little change in drop diameter, while those that exhibit Newtonian rheology or are shear-thickening will exhibit a significant increase in drop size.

A more quantitative measure of rheology is measurement of viscosity as a function of shear force by use of a viscometer. A common viscometer for such use is a Brookfield Dial Reading Viscometer, which is routinely used for viscometric measurement of liquids (see http://www.brookfieldengineering.com/products/viscometers/laboratory-dial-reading.asp and http://www.viscometers.org/PDF/Manuals/laboratory/DIAL.PDF). A standardized element is submerged in a liquid contained in a vessel, and a rotational shear force is applied. The Dial Viscometer measures the torque necessary to overcome the viscous resistance to the induced movement. This is accomplished by driving the immersed element, which is called a spindle, through a beryllium copper spring. The degree to which the spring is wound is proportional to the viscosity of the fluid. The viscometer is able to measure over a number of ranges since, for a given spring deflection, the actual viscosity is proportional to the spindle speed and is related to the spindle's size and shape. For a material of given viscosity, the resistance will be greater as the spindle size and/or rotational speed increase. The minimum viscosity range is obtained by using the largest spindle at the highest speed; the maximum range by using the smallest spindle at the slowest speed.

A common method for characterizing non-Newtonian flow is to compute the ratio of the fluid's viscosities as measured at two different speeds with the same spindle. These measurements are usually made at speeds that differ by a factor of 10 (2 and 20 RPM, or 10 and 100 RPM). In constructing the ratio, the viscosity value at the lower is placed in the numerator, and the one at the higher speed in the denominator. For pseudoplastic fluids the ratio exceeds 1.0 as the degree of pseudoplastic behavior increases. For dilatant fluids, the ratio is less than 1.0 as the degree of dilatancy increases. For the purposes herein, it is preferred to have a viscosity/shear rate ratio greater than 1.0, more preferably greater than 2.0, and most preferably greater than 4.0.

A formulation was made up according to the following criteria:

Formulation 1

| Ingredient | Weight Percent |
| --- | --- |
| Dimethicone, 500 cp | 50.00% |
| Isopropyl myristate | 35.50% |
| Nonionic surfactant | 10.00% |
| Polyamide thickener | 3.50% |
| Fragrance | 1.00% |
| Colorant | trace |

The finished product was evaluated versus a commercial 500 cp dimethicone via the Zahn cup method and tilt drop test, the result to be found in Table 2 below.

TABLE 2

RHEOLOGY

| Sample | Efflux Time (sec)[a] | Drop size (cm)[b] | | Percent Increase |
| --- | --- | --- | --- | --- |
| | | Before | After | |
| Formulation 1 | 27 | 0.90 | 1.15 | 28% |
| Commercial dimethicone, 500 cp | 94 | 1.08 | 2.17 | 101% |

Notes to TABLE 2
[a]Modified Zahn Cup #4 test, efflux time is time elapsed until stream is no longer continuous
[b]Drop size measured at rest, and after a 20° tilting for one minute.

Formulation 1 was further evaluated for its viscosity over a range of shear rates using a Brookfield LVT Dial Reading Viscometer; see results in FIG. 1 and TABLE 3, below. The formulation exhibited high viscosity at low shear rates, which then decreased sharply towards higher shear rates. Such behavior is indicative of pseudoplasticity, and in particular, Bingham plastics. In Formulation 1, when the viscosity measured at low shear rate, for example at 3 rpm, is compared to the viscosity measured at a higher shear rate, for example at 30 rpm, a significant difference in measured viscosities is seen: a ratio of viscosities at low shear rate to high shear rate—its viscosity/shear rate ratio—is significantly greater than 1. In contrast, a commercially available polydimethylsiloxane (Andisil® SF 500, a 500 centipoise dimethicone) was measured. As expected, its viscosity was essentially invariant over the range of rotational speeds evaluated, and its viscosity/shear rate ratio was essentially 1.0.

TABLE 3

VISCOMETRIC EVALUATION OF FORMULATION 1 AND OF COMMERCIALLY AVAILABLE POLYDIMETHYLSILOXANE

| Shear Rate (rpm) | Formulation 1 Viscosity (cp) | Commercial Dimethicone Viscosity (cp) |
| --- | --- | --- |
| 0.6 | 9800[c] | 500[a] |
| 1.5 | 4800[c] | 500[a] |
| 3 | 2800[c] | 490[a] |
| 6 | 1700[c] | 495[a] |
| 6 | 1620[b] | 520[b] |
| 12 | 1050[b] | 513[b] |
| 30 | 650[b] | 500[b] |

Notes to TABLE 3
Measurements taken on a Brookfield LVT Dial Reading Viscometer
[a]As measured using Spindle 1
[b]As measured using Spindle 2
[c]As measured using Spindle 3

In this case, we compare the viscosity/shear rate ratios of Formulation 1 and of the commercially available polydimethylsiloxane, for example at shear rates of 3 and 30 rpm. The ratio of the viscosities of polydimethylsiloxane is at these two shear rates is 490/500 (essentially 1.0), while that of Formulation 1 is 2800/650=4. The results from the above tests indicate that the compositions exhibit pseudoplasticity, that is, they flow readily through dispensing means such as the sample dispenser/applicator described herein, and when shear stress is eliminated, the compositions will cease to flow. In practice, this was in fact shown to be the case: the composition was easily and controllably delivered by the dispensing means herein described.

Methodology

Compositions of the present disclosure are applied to the hair and skin of a subject and are permitted to remain on the subject for some amount of time. The amount of time will depend on whether or not the subject is currently experiencing an ectoparasite infestation, and how severe that infestation may be. Because the inventive ingredients are of relatively low toxicity, the compositions can be left on test subjects for as long as desired, even hours. However, the effectiveness of the formulation is such that the formulation is unlikely to need to remain on the subject for more than about ten minutes. The compositions of the instant disclosure may be left on a subject for longer periods of time, and/or they may be applied over the course of multiple treatments.

According to one embodiment, the nonaqueous, non-Newtonian compositions presented herein can be applied directly to a subject requiring treatment for ectoparasite infestations. According to another embodiment, an implement such as a comb, brush, applicator or other device may be used to deliver the inventive compositions to a subject. Regardless of how the compositions presented herein are delivered to the hair and skin of a subject, it is desired that the compositions coat a region experiencing an ectoparasite infestation as completely as possible, in order to most efficiently kill the particular pest.

Sample Dispenser/Applicator

One example of an applicator that may be used for the delivery of compositions of the instant disclosure is shown at 100 in FIG. 1. Dispenser-applicator 100 includes handle or grip portion 102, contour region 104 and applicator region 106. Handle portion 102 is hollow, and further includes first attachment means 108 (not shown) disposed towards the interior of handle 102. First attachment means 108 comprises at least one attaching component 110 (not shown) for matingly engaging with container 112 (not shown). Examples of attaching components 110 include, but are not necessarily limited to threads, tabs, compression fittings, slip joints, snap fasteners, and the like. Container 112, in turn, represents any generic type of reservoir that can provide any of the topical, nonaqueous compositions described herein for use to a subject. Examples of containers that are contemplated for use herein include, but are not necessarily limited to, tubes, soft-sided bottles, pouches, sleeves, bottles or jars with pistons or discharge means, etc. It is also envisioned that a container may have a means of attachment appropriate for a bottle containing the inventive compositions under pressurized gas such as air, nitrogen, carbon dioxide, volatile hydrocarbons, or other gas.

First attachment means 108 matingly engages at least one feature of container 112 comprising second attachment means 114 (not shown). Second attachment means 114 therefore comprises a matingly configured component for use in engaging first attachment means 108, such that the topical compositions described herein may be delivered from container 112 to dispenser 100 without loss of any of the composition being delivered. Examples of second attachment means 114 include, but are not necessarily limited to threads, tabs, compression fittings, slip joints snap fasteners, and the like. Cutouts 116 on each side of handle 102, only one of which is shown in FIG. 1, create leg sections 118 that are useful for guiding container 112 into proper mating position with dispenser 100.

Once container 112 is attached to dispenser 100, an aliquot of a topical composition according to the instant disclosure can be expressed into dispenser 100. Contour region 104 conducts the aliquot towards applicator region 106 of dispenser 100 via channel 120 (not shown), which is disposed towards the interior of applicator region 106. Channel 120, in turn, has openings 122 (not shown) between teeth 124. Teeth 124 extend outwards perpendicularly from, and are arranged in linear fashion along, first facing surface 126 of applicator region 106 of dispenser 100. Collectively, teeth 124 are said to comprise rake portion 132 of dispenser 100.

Along a second facing surface 128 that is disposed at some distance away from first facing surface 126, a plurality of tines 130 that collectively comprise comb portion 134 are situated. Unlike the openings 122 that are found between teeth 124 along first facing surface 126, there are no openings between tines 130 of comb portion 134 along second facing surface 128. Accordingly, compositions that are dispensed from container 112 are expressed only along first facing surface 126 of dispenser 100. As will be understood by those skilled in the relevant art, the angle that is formed along applicator region 106 between rake portion 132 and comb portion 134 may have any value, although angles of at least 90° are preferred, while angles from about 120° to about 180° are especially preferred.

During use of a dispenser-applicator to apply a composition according to the instant disclosure, a slight amount of pressure applied to container 112 will cause an aliquot to be expressed from container 112 and enter channel 120, such that it is dispensed through openings 122 of applicator region 106 between teeth 124. Note that teeth 124 are configured to allow convenient application of the composition to the hair-containing skin of an individual and move the composition along the skin, without eliminating it as applicator 100 passes over skin or among hairs of a subject. There are no restrictions anticipated as to the shape or displacement of teeth 124 versus that of tines 130. However, as teeth 124 function to dispense the composition and disperse it onto affected hair strands without flow restriction, it may be advantageous for teeth 124 to be more coarsely distributed than tines 130.

Once the region of an ectoparasite infestation is thoroughly covered with composition, the material is permitted to remain on the subject for a period of time. Once it has been determined that an adequate time for treatment has been achieved, the hair is combed with tines 130 of comb portion 134 to remove the ectoparasites, including adults, juveniles, and eggs. For this purpose, it is anticipated to be appropriate for individual tines 130 will be placed in close proximity to one another. It is envisioned that it may be advantageous for individual tines 130 to be separated by a distance approximately equal to the diameter of a human hair, in order to remove even the smallest ova or nits of ectoparasite pests from a subject most effectively. It is yet further envisioned that tines 130 are shaped so as to maximize their ability to fairly scrape the ectoparasites from the affected hair, for example a shape resembling a diamond in cross-section. Subsequently, following treatment and removal of ectoparasites, the composition is rinsed from the hair or skin of the individual.

In the course of developing the topical compositions presented herein, it was advantageously found that compositions could be provided in a form that is non-Newtonian. That is, once a force was no longer applied to cause the compositions to flow, movement of the composition would cease. In other words, regardless of the direction or orientation in which dispenser 100 is held with respect to an individual subject, once force is no longer applied to container 112, the treatment composition ceases to be expressed from dispenser 100. This non-Newtonian feature has resulted in great acceptance and desirability of the compositions as disclosed and described herein. The fact that the compositions do not continue to flow undiminished when force is no longer applied to a container means that there is less mess, less undesired expression or expulsion of product from its container, and greater convenience in directing and using the compositions with subjects.

It is to be noted that the aforementioned discussion of a preferred dispenser is not intended to limit the range or type of dispensers appropriate for delivering the compositions presented herein. Indeed, any dispenser designed for controlled delivery of liquid compositions may be appropriate for the purpose of this invention.

Experimental Section

A number of methods were used to evaluate the effectiveness of the inventive compositions against ectoparasites. As described below in the examples, they include a screening process for purposes of evaluating commercially available products as well as formulation variables, a semi-clinical confirmatory process of a preferred composition, and a clinical test of a preferred composition.

Inventive compositions were evaluated for controlled delivery versus commercial products, in a dispensing means such as described herein (see FIG. 1). Compositions were also tested for ease of risibility versus commercial products, as discussed below.

EXAMPLES

Example 1

In one procedure that provides an evaluative method for determining effectiveness of commercial products, live parasites were removed from subjects' hair and placed into a Petri dish. One to two drops of test formulation were placed upon the test insect, most commonly a louse. The specimen was observed under magnification for initial movement, and was kept under observation for up to fifteen additional minutes. Lice may initially cease movement, yet resume movement after an initial recovery period, hence while effectiveness can sometimes be ascertained after as little as one minutes, the extended observation is necessary in order to confirm that a particular louse is deceased. The effectiveness of the treatment was then rated on a 0-4 scale, with a score of 0 denoting total ineffectiveness and a score of 4 denoting total kill.

The results of the screening test are summarized below in Table 4.

TABLE 4

EVALUATION OF COMMERCIAL PRODUCTS

| Product | Efficacy[a] Score | Results | Active Material |
| --- | --- | --- | --- |
| Lice MD | 4 | Dead <1 minute | 100% dimethicone |
| Rapunzel's Extra Strength Lice Neutralizer | 4 | Dead <1 minute | 100% dimethicone (blend) |
| I Hate Lice | 4 | Dead <5 minutes | 50% dimethicone, 50% olive oil |

TABLE 4-continued

EVALUATION OF COMMERCIAL PRODUCTS

| Product | Efficacy[a] Score | Results | Active Material |
|---|---|---|---|
| Licenders Lice Shampoo | 4 | Dead <3 minutes | Enzymes (water-based formula) |
| Hair Fairies Nit-Zapping™ Clenz Cream | 3 | Dead <10 minutes | Dimethiconol, essential oils (water-based formula) |
| Vamousse Lice Treatment | 3 | Dead <15 minutes | Isopropyl alcohol, isopropyl myristate, natrum muriaticum (water-based formula) |
| Nix Lice Killing Creme Rinse | 2 | Some dead, some survived after 10 minutes | Permethrin (water-based formula) |
| Soft Soap | 2 | Some dead, some survived after 15 minutes | None (surfactants, water-based formula) |
| ByeByeNits Anti-Lice Cream | 0 | Moved slower, no kill | Essential oils (surfactants, water-based formula) |
| Germ-X | 0 | No effect | None (surfactants, water-based formula) |
| Water | 0 | No effect | None (control) |

Notes to TABLE 4
[a]Efficacy was evaluated on a scale from 1 to 4 following treatment with the commercial product as follows:
4 = Elimination of 100% of all live lice within 5 minutes;
3 = Elimination of 75% of live lice within 5 minutes (25% live lice remain);
2 = Elimination of 50% of live lice after 5 minutes (50% live lice remain);
1 = Elimination of 25% of lice after 5 minutes (75% live lice remain); and
0 = No elimination of live lice after 5 minutes (100% live lice remain).

This commercial product screening revealed that the most effective products were based on dimethicone, most preferably without significant levels of water.

Example 2

An evaluation of formulation variables was undertaken, using the method described in Example 1. Studies of the effect of water on killing efficacy of several formulations were undertaken, in order to establish baseline information for possible use with formulations presented herein. Accordingly, various levels of water were evaluated; significant levels of water inhibited the pesticidal efficacy of all formulas. The results are shown in TABLE 5 below.

TABLE 5

EVALUATION OF WATER CONTENT

| Ex. No. | Water | PDMS[a] | Surfactant | Solvent | Thickener | Ethanolamine | Efficacy[g] Score |
|---|---|---|---|---|---|---|---|
| C1 | 84.5 | 0.0 | 10.0[b] | — | 5.0[e] | 0.5 | 0 |
| C2 | 83.5 | 5.0 | 10.0[b] | — | 1.0[e] | 0.5 | 0 |
| C3 | 78.5 | 10.0 | 10.0[b] | — | 1.0[e] | 0.5 | 0 |
| C4 | 63.5 | 25.0 | 10.0[b] | — | 1.0[e] | 0.5 | 0 |
| C5 | 38.5 | 50.0 | 10.0[b] | — | 1.0[e] | 0.5 | 0 |
| C6 | 39.0 | 50.0 | 10.0[b] | — | 0.5[e] | 0.5 | 0 |
| 1 | 0.0 | 50.0 | 10.0[c] | 36.5[d] | 3.5[f] | 3.5 | 4 |

Notes to TABLE 5
1. All amounts are expressed in terms percent by weight, or wt. %.
[a]Polydimethylsiloxane, 350 cp
[b]C$_{9-11}$ alcohol ethoxylate (8EO)
[c]C$_{12-15}$ alcohol ethoxylate (7EO)
[d]Isopropyl myristate
[e]Polyacrylate-based thickener
[f]Polyamide-based thickener
[g]Efficacy was evaluated on a scale from 1 to 4 following treatment as follows:
4 = Elimination of 100% of all live lice within 5 minutes;
3 = Elimination of 75% of live lice within 5 minutes (25% live lice remain);
2 = Elimination of 50% of live lice after 5 minutes (50% live lice remain);
1 = Elimination of 25% of lice after 5 minutes (75% live lice remain); and
0 = No elimination of live lice after 5 minutes (100% live lice remain).

Example 3

An evaluation of formulation variables was undertaken, using the method described in Example 1. Studies of the possible killing efficacy of several solvents were undertaken, in order to establish baseline information for possible use with formulations presented herein. Accordingly, various types of solvents were evaluated. The results are shown in Table 6 below.

TABLE 6

EVALUATION OF SOLVENTS

| Example No. | Butyl 3-hydroxybutyrate | Isopropyl myristate | Propylene glycol | PDMS | Surfactant[d] | Polyamide thickener | Efficacy[e] Score |
|---|---|---|---|---|---|---|---|
| B1 | 100 | | | | | | 0 |
| B2 | 50.0 | | | 50[a] | | | 4 |
| B3 | 50.0 | | | 50[b] | | | 4 |
| B4 | 35.0 | | | 50[c] | 10 | 5.0 | 4 |
| B5 | 32.5 | | | 50[c] | 10 | 7.5 | 4 |
| B6 | 32.5 | | | 50[c] | 10 | 7.5 | 4 |
| B7 | | 36.5 | | 50[c] | 10 | 3.5 | 4 |
| B8 | | 35.0 | | 50[c] | | 5.0 | 4 |
| B9 | | | 35.0 | 50[c] | 10 | 5.0 | 4 |
| B10 | | | 32.5 | 50[c] | 10 | 7.5 | 4 |

Notes to TABLE 6
1. All amounts are expressed in terms percent by weight, or wt. %.
[a]Polydimethylsiloxane, 350 cp
[b]Polydimethylsiloxane, 1000 cp
[c]Polydimethylsiloxane, 500 cp
[d]C$_{12-15}$ alcohol ethoxylate (7EO)
[e]Efficacy was evaluated on a scale from 1 to 4 following treatment as follows:
4 = Elimination of 100% of all live lice within 5 minutes;
3 = Elimination of 75% of live lice within 5 minutes (25% live lice remain);
2 = Elimination of 50% of live lice after 5 minutes (50% live lice remain);
1 = Elimination of 25% of lice after 5 minutes (75% live lice remain); and
0 = No elimination of live lice after 5 minutes (100% live lice remain).

Example 4

In a second procedure that provides a more refined screening method for effectiveness, live head lice, or *Pediculus humanus capitis*, were obtained from an external organization that uses a vacuum collection method to remove lice from people with infestations. Both female and male adult head lice were used. Upon collection, the head lice were examined and only fully active lice were used for testing. Lice were housed under optimal environmental conditions of 25±2° C. and 80% relative humidity at all times. Ten head lice, a mixture of adults and nymphs, were placed onto a hair bundle. The hair bundle was treated with the product by pulling the hair bundle through a consistent amount of treatment composition, ensuring complete coverage of hair and lice. The hair bundle was weighed before and after treatment to determine the amount of applied product. The hair bundle and head lice were then placed on Petri dishes with a filter paper moistened with 200 µL of water to prevent them from desiccating. The product was left on the hair bundle for 10 minutes. Hair bundles were then rinsed with distilled water and placed into a clean Petri dish with new, moistened filter paper. Head lice vitality was assessed by classifying each louse into the applicable vitality category. All lice were examined by the same observer to minimize observer variation. Head lice that scored a 3 or 4, indicating only minor indications of vital signs present or none whatsoever, respectively, were categorized as dead for reporting purposes. The results are presented in TABLE 7.

TABLE 7

PERCENTAGE MORTALITY OF HEAD LICE

| Time Point | Treated (1) | Treated (2) | Control (1) | Control (2) |
| --- | --- | --- | --- | --- |
| 10 minutes | 100% | 100% | 0% | 0% |
| 20 minutes | 100% | 100% | 10% | 0% |
| 30 minutes | 100% | 100% | — | 0% |
| 1 hour | 100% | 100% | 10% | 0% |
| 3 hours | 100% | 100% | 10% | 0% |
| 6 hours | 100% | — | 50% | — |
| 19 hours | — | 100% | — | 20% |

One hundred percent of lice treated with the pediculicide gel showed only minor or no vital signs (score of 3 or 4, respectively) as determined 10 minutes post-treatment. Lice treated with water only, as a negative control, showed complete vital signs after 10 minutes, 10% mortality after 3 hours and 50% mortality after 6 hours. In the second control test, no mortality was observed for the first 3 hours of the test and only 20% mortality after 19 hours.

Example 5

In yet another procedure that provides real-life evaluation of effectiveness, a composition according to Formulation 1 was assessed in a commercial clinical operation. Using one type of dispensing means consistent with dispenser or applicator 100 shown in FIG. 1, the composition was applied to the heads of test subjects that had been diagnosed to have head lice infestation. The composition was allowed to stay on the subjects' heads for ten minutes, followed by combing with the fine tines of the dispensing means, and rinsing. Lice recovered from combing were evaluated for viability, and found to be dead, resulting in a score of 4. Moreover, there were no viable lice remaining in the scalp of the test subjects.

Example 6

Inventive compositions were evaluated for convenience in use and the ability to control delivery through a dispensing means such as the tool shown in FIG. 1 above, versus commercially available products. In using the dispenser/applicator of FIG. 1, an inventive composition did not begin flowing through openings 122 of dispenser/applicator 100 until a shear force, such as squeezing of a bottle or container 112 to which dispenser/applicator 100 was affixed, was applied. Once the application of shear force ceased, the flow of inventive compositions slowed and stopped altogether within seconds. By contrast, it was found that when a commercially available product comprising pure dimethicone, 350 cp, was used in combination with dispenser/applicator 100, flow of the product commenced even before the bottle containing the product was squeezed. Moreover, and in contrast to the compositions of the instant disclosure, flow of the commercially-available product out through the device continued, even after cessation of applied stress. Surprisingly, even samples of neat higher-viscosity dimethicones were found to flow uncontrollably out from dispenser/applicator means 100, in that flow of the liquid dimethicones commenced even before squeezing the bottle that contained the liquid dimethicone, and the dimethicones continued to flow out through openings 122 even after cessation of shear stress.

Example 7

A batch of topical, nonaqueous non-Newtonian composition according to the disclosure was prepared and tested by a panel of individuals for risibility compared to a commercially available product comprised solely of 350 cp dimethicone. The testing technique employed was as follows. A sample of about three milliliters of formulation prepared according to the instant disclosure was introduced onto one hand of each of twenty-one test subjects. Onto the other hand of each test individual was introduced three milliliters of a commercially available product. The individuals then rubbed the fingers of each hand together, in order to more completely distribute the formulation present on that particular hand. The test subjects then placed their hands under running water and were asked to report how rapidly the formulas rinsed from each of their hands.

All twenty-one individuals rated the inventive composition to be significantly better at rinsing from their hands as compared to the test dimethicones alone. For the most part, each test subject reported requiring less than about ten seconds in order to completely rinse the composition of the instant disclosure from a hand, without any need for additional soap. By contrast, each of the twenty-one individuals reported that the commercially available product never rinsed off their hand with plain water. Rather, the use of an additional soap in combination with several minutes' of actively cleaning the hand was necessary in order to completely remove the commercially available product from their skin.

Example 8

In yet another use for the inventive composition, a composition according to Formulation 1 is used to treat a canine carrying multiple brown dog ticks, or *Rhipicephalus sanguineus*. The inventive composition is applied directly to the ticks and allowed to remain in place for ten minutes. After treatment, the ticks are removed from the animal and are presumed to be dead.

Example 9

In treating a dog with an infestation of fleas, *Ctenocephalides canis*, a quantity of the inventive composition is applied directly and liberally over the dog's body, while avoiding sensitive areas such as the eyes, nose and mouth, and is worked down to the skin of the animal with a coarse comb. The composition is allowed to remain in place for ten minutes. A fine-toothed comb such as a flea comb is used to ensure overall coverage of the animal. Subsequent to treatment, the composition is easily rinsed off from the dog and the hands of the handler. All fleas found in the washbasin or subsequently remaining on the dog are shown to be dead.

A series of representative compositions that may be prepared according to the instant disclosure are tabulated and presented in TABLE 8.

TABLE 8

REPRESENTATIVE COMPOSITIONS

| Ex. No. | Dimethicone (10 cps) | Dimethicone (500 cps) | Dimethicone (1000 cps) | Dimethicone (10,000 cps) | Dimethicone (100,000 cps) | Isopropyl myristate | Butyl 3-hydroxy-butyrate | Propylene glycol | $C_{9-11}$ alcohol ethoxylate (8EO) |
|---|---|---|---|---|---|---|---|---|---|
| 10 | 10.0 | | | | | 60.0 | | | 26.0 |
| 11 | 25.0 | | | | | | 58.5 | | |
| 12 | 50.0 | | | | | | | 21.0 | |
| 13 | 75.0 | | | | | 11.0 | | | |
| 14 | | 10.0 | | | | 60.0 | | | 26.0 |
| 15 | | 25.0 | | | | | 58.5 | | |
| 16 | | 50.0 | | | | | | 21.0 | |
| 17 | | 75.0 | | | | 11.0 | | | |
| 18 | | | 10.0 | | | 60.0 | | | 26.0 |
| 19 | | | 25.0 | | | | 58.5 | | |
| 20 | | | 50.0 | | | | | 21.0 | |
| 21 | | | 75.0 | | | 11.0 | | | |
| 22 | | | | 10.0 | | 60.0 | | | 26.0 |
| 23 | | | | 25.0 | | | 58.5 | | |
| 24 | | | | 50.0 | | | | 21.0 | |
| 25 | | | | 75.0 | | 11.0 | | | |
| 26 | | | | | 10.0 | 60.0 | | | 26.0 |
| 27 | | | | | 25.0 | | 58.5 | | |
| 28 | | | | | 50.0 | | | 21.0 | |
| 29 | | | | | 75.0 | 11.0 | | | |

| Ex. No. | $C_{12-15}$ alcohol ethoxylate (4EO) | $C_{12-15}$ alcohol ethoxylate (7EO) | Sorbitan monolaurate | Polyamide thickener, ester-terminated #1 | Polyamide thickener, ester-terminated #2 | Polyamide thickener, amide-terminated | Perfume | Colorant |
|---|---|---|---|---|---|---|---|---|
| 10 | | | | 2.5 | | | 1 | 0.5 |
| 11 | 10.0 | | | | 5.0 | | 1 | 0.5 |
| 12 | | 20.0 | | | | 7.5 | 1 | 0.5 |
| 13 | | | 10.0 | 2.5 | | | 1 | 0.5 |
| 14 | | | | 2.5 | | | 1 | 0.5 |
| 15 | 10.0 | | | | 5.0 | | 1 | 0.5 |
| 16 | | 20.0 | | | | 7.5 | 1 | 0.5 |
| 17 | | | 10.0 | 2.5 | | | 1 | 0.5 |
| 18 | | | | 2.5 | | | 1 | 0.5 |
| 19 | 10.0 | | | | 5.0 | | 1 | 0.5 |
| 20 | | 20.0 | | | | 7.5 | 1 | 0.5 |
| 21 | | | 10.0 | 2.5 | | | 1 | 0.5 |
| 22 | | | | 2.5 | | | 1 | 0.5 |
| 23 | 10.0 | | | | 5.0 | | 1 | 0.5 |
| 24 | | 20.0 | | | | 7.5 | 1 | 0.5 |
| 25 | | | 10.0 | 2.5 | | | 1 | 0.5 |
| 26 | | | | 2.5 | | | 1 | 0.5 |
| 27 | 10.0 | | | | 5.0 | | 1 | 0.5 |
| 28 | | 20.0 | | | | 7.5 | 1 | 0.5 |
| 29 | | | 10.0 | 2.5 | | | 1 | 0.5 |

Note to TABLE 8
1. All amounts are expressed in terms of percent by weight, or wt. %.

Kits

In one aspect, the foregoing discussions describe formulations and techniques for using and applying the compositions and formulations presented herein. In addition to providing the compositions for use as formulated products, according to alternate embodiments, the compositions presented herein may also be provided as part of a kit that includes instructions and hints or suggestions for application and use of the compositions. In yet alternate embodiments, the compositions presented herein may be offered as part of a kit that includes and applicator or dispenser for applying the composition to a subject along with instructions and/or hints for using both the composition and the dispenser. Other combinations of kits and components thereof that are consistent with the compositions and dispenser/applicator means presented herein are also contemplated.

The foregoing Examples demonstrate several embodiments whereby the compositions and methods of the present disclosure provide nonaqueous topical compositions for use on the hair of animals or humans. In addition, a number of examples are presented that embody various methods of use of the nonaqueous topical compositions presented herein. These methods further demonstrate the beneficial attributes of the disclosed compositions when used in the course of treatment and eradication of certain pest infestations, such as lice, nits, fleas, ticks and the like/head lice, body lice and pubic lice. Kits containing the disclosed compositions and instructions for their use, either with or without an applicator or dispenser for the compositions, are also disclosed.

The present disclosure includes detailed descriptions embodiments as well as additional information in the form of Structures, Figures, Tables and Examples. Any specific embodiments should not be construed as narrowing the scope of the disclosure, but rather as illustrative examples. Although preferred embodiments of the disclosure may be specifically described above, it is to be understood that various modifications and substitutions are anticipated and may be made to the described compositions, materials, dispenser or applicator, kits, and methods of use, without departing from the broad spirit or scope of the embodiments contemplated herein. Various examples of non-limiting embodiments of the instant disclosure are further provided and described in the claims, which follow.

What is claimed is:

1. A nonaqueous composition for the control and elimination of ectoparasites on a subject, comprising:
    a. at least one active ingredient;
    b. at least one emulsifier; and
    c. at least one thickener;
    wherein the at least one active ingredient comprises a polydimethylsiloxane and the composition is non-Newtonian, wherein the at least one thickener is a polymeric amide, and the composition is a Bingham plastic, and wherein the composition is essentially free of a cyclic dimethicone.

2. The nonaqueous composition of claim 1, wherein the ectoparasite is selected from the group consisting of lice, nits, ticks, fleas and combinations of any of the foregoing, and wherein the composition exhibits pseudoplastic rheology.

3. The nonaqueous composition of claim 1, wherein the ectoparasite is selected from the group consisting of *Pediculus capitis, Pediculus humanus capitis* or head lice, *Pediculus corporis, Pediculus humanus corporis* or body lice, *Phthirus pubis* or pubic lice or crabs, *Rhipicephalus sanguineus* or brown dog ticks, *Ctenocephalides canis* or canine fleas or fleas.

4. The nonaqueous composition of claim 3, wherein the ectoparasite is *Pediculus humanus capitis*.

5. The nonaqueous composition of claim 1, wherein the polydimethylsiloxane has a viscosity not greater than 100,000 cps and wherein the composition is readily rinsible.

6. The nonaqueous composition of claim 1, wherein the at least one emulsifier is selected from the group consisting of anionic surfactants, nonionic surfactants, amphoteric surfactants, cationic surfactants and combinations of any of the foregoing.

7. The nonaqueous composition of claim 6, wherein the at least one emulsifier is a nonionic surfactant.

8. The nonaqueous composition of claim 7, wherein the nonionic surfactant comprises an alcohol alkoxylate, an alcohol ethoxylate, as well as combinations of any of the foregoing.

9. The nonaqueous composition of claim 1, wherein the nonaqueous solvent is selected from the group consisting of C1-C6 alkanols, C1-C6 diols, C1-C1o alkyl ethers of alkylene glycols, C3-C24 alkylene glycol ethers, polyalkylene glycols, short chain carboxylic acids, short chain esters, isoparaffinic hydrocarbons, mineral spirits, alkylaromatics, terpenes, terpene derivatives, terpenoids, terpenoid derivatives, formaldehyde, pyrrolidones, as well as combinations of any of the foregoing.

10. The composition of claim 1, wherein the polymeric amide is selected from the group consisting of ester-terminated polyamides, amide-terminated polyamides, ether-terminated polyamides, and combinations of any of the foregoing.

11. A nonaqueous, non-Newtonian composition for the control and elimination of ectoparasites on a subject, comprising:
    a. at least one active ingredient;
    b. at least one surfactant;
    c. at least one nonaqueous solvent; and
    d. at least one thickener; and
    e. at least one colorant, at least one fragrance, or at least one colorant and at least one fragrance;
    wherein the at least one surfactant is selected from the group consisting of alcohol alkoxylates, alcohol ethoxylates, as well as combinations of any of the foregoing;
    wherein the at least one nonaqueous solvent is selected from the group consisting of C1-C6 alkanols, C1-C6 diols, C1-C1o alkyl ethers of alkylene glycols, C3-C24 alkylene glycol ethers, polyalkylene glycols, short chain carboxylic acids, short chain esters, isoparaffinic hydrocarbons, mineral spirits, alkylaromatics, terpenes, terpene derivatives, terpenoids, terpenoid derivatives, formaldehyde, pyrrolidones, as well as combinations of any of the foregoing;
    wherein the at least one thickener is a polymeric amide selected from the group consisting of ester-terminated polyamides, amide-terminated polyamides, ether-terminated polyamides, and combinations of any of the foregoing; and
    wherein the at least one active ingredient comprises a polydimethylsiloxane, and wherein the active ingredient lacks a cyclic dimethicone.

12. The nonaqueous, non-Newtonian composition of claim 11, wherein the ectoparasite is selected from the group consisting of lice, nits, ticks, fleas and combinations of any of the foregoing, and wherein the polydimethylsiloxane has a viscosity not greater than about 100,000 cps.

13. The nonaqueous, non-Newtonian composition of claim 11, further wherein the at least one colorant comprises a pigment or a lake, and wherein the at least one fragrance has an octanol/water partitioning coefficient of about 1,000 or smaller.

\* \* \* \* \*